US009895550B2

(12) United States Patent
Williams et al.

(10) Patent No.: US 9,895,550 B2
(45) Date of Patent: Feb. 20, 2018

(54) FLEXIBLE LED LIGHT PAD FOR PHOTOTHERAPY

(71) Applicant: Applied BioPhotonics Limited, Cupertino, CA (US)

(72) Inventors: Richard K. Williams, Cupertino, CA (US); Keng Hung Lin, Chupei (TW); Yu-Min Lin, Kaohsiung (TW); Daniel Schell, Los Gatos, CA (US); Joseph Leahy, Los Gatos, CA (US)

(73) Assignee: Applied BioPhotonics Ltd, Hong Kong (CN)

(*) Notice: Subject to any disclaimer, the term of this patent is extended or adjusted under 35 U.S.C. 154(b) by 337 days.

(21) Appl. No.: 14/460,638

(22) Filed: Aug. 15, 2014

(65) Prior Publication Data

US 2015/0202455 A1 Jul. 23, 2015

Related U.S. Application Data

(60) Provisional application No. 61/930,856, filed on Jan. 23, 2014.

(51) Int. Cl.
*A61N 5/06* (2006.01)
*F21V 23/06* (2006.01)
*F21V 23/00* (2015.01)

(52) U.S. Cl.
CPC ........ *A61N 5/06* (2013.01); *A61N 2005/0645* (2013.01); *A61N 2005/0652* (2013.01)

(58) Field of Classification Search
CPC .... A61N 2005/0645; A61N 2005/0652; A61N 5/06

See application file for complete search history.

(56) References Cited

U.S. PATENT DOCUMENTS

| 8,801,254 | B2* | 8/2014 | McNeill | ................. | A61N 5/062 |
|---|---|---|---|---|---|
| | | | | | 362/249.04 |
| 2008/0269849 | A1* | 10/2008 | Lewis | .................. | A61N 5/0613 |
| | | | | | 607/91 |

* cited by examiner

*Primary Examiner* — Scott T Luan
(74) *Attorney, Agent, or Firm* — Patentability Associates; David E. Steuber

(57) ABSTRACT

In a flexible LED pad for use in phototherapy treatment of humans or animals, the PCBs in the pad are securely linked together with electrical connectors and ribbon cables to prevent the connections from being broken as the flexible pad is bent or otherwise deformed during the treatment. In one embodiment, low-profile socket connectors are mounted to the PCBs and mate with plug connectors at the ends of the ribbon cables. For similar reasons, the LED pad may be connected to an LED control unit by means of an electrical connector (e.g. a USB socket) mounted to a PCB in the LED pad. The PCBs, on which the LEDs are mounted, are fitted into a downset in the flexible pad to prevent the LEDs from becoming misaligned with openings in the flexible pad.

26 Claims, 50 Drawing Sheets

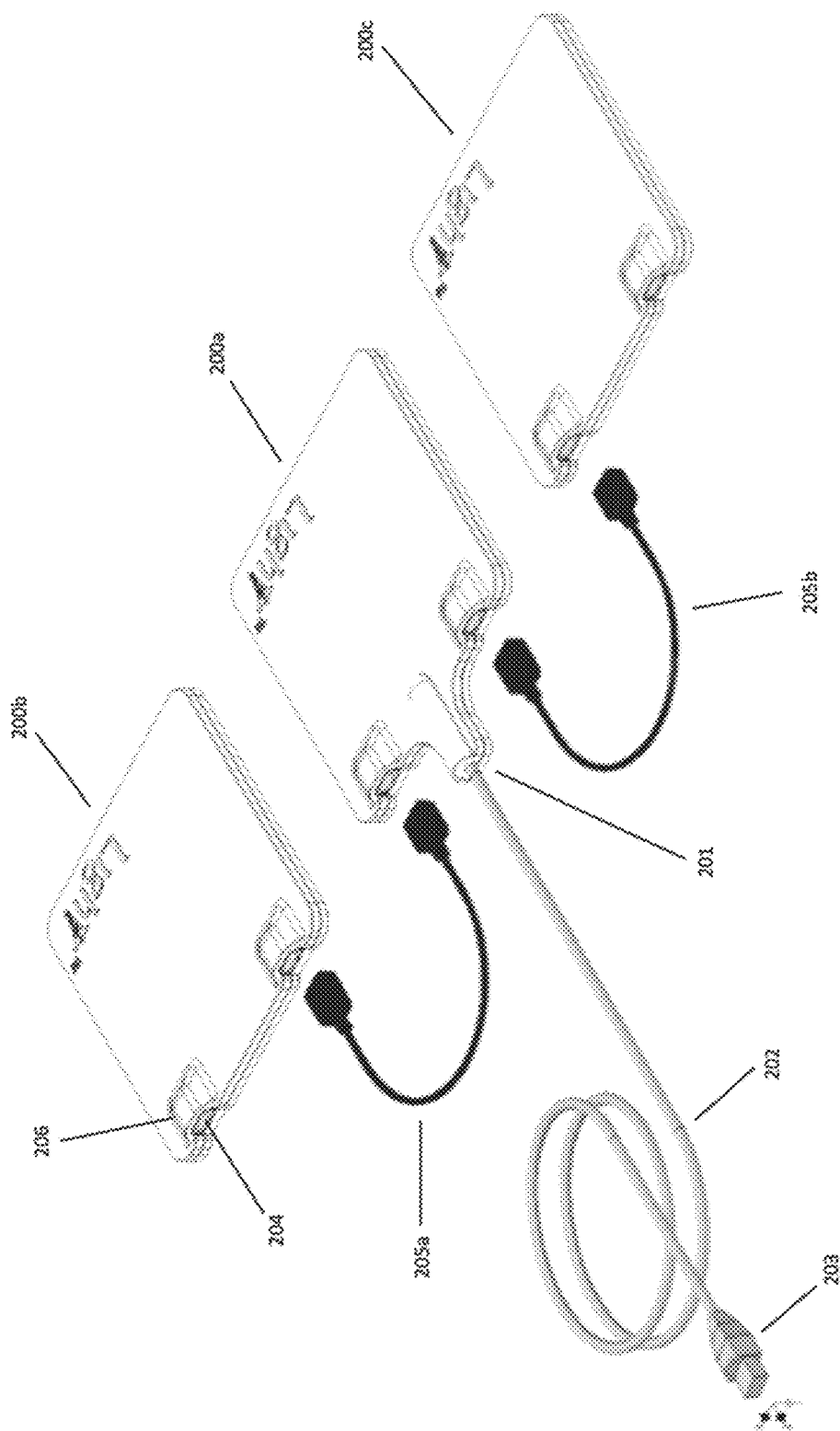

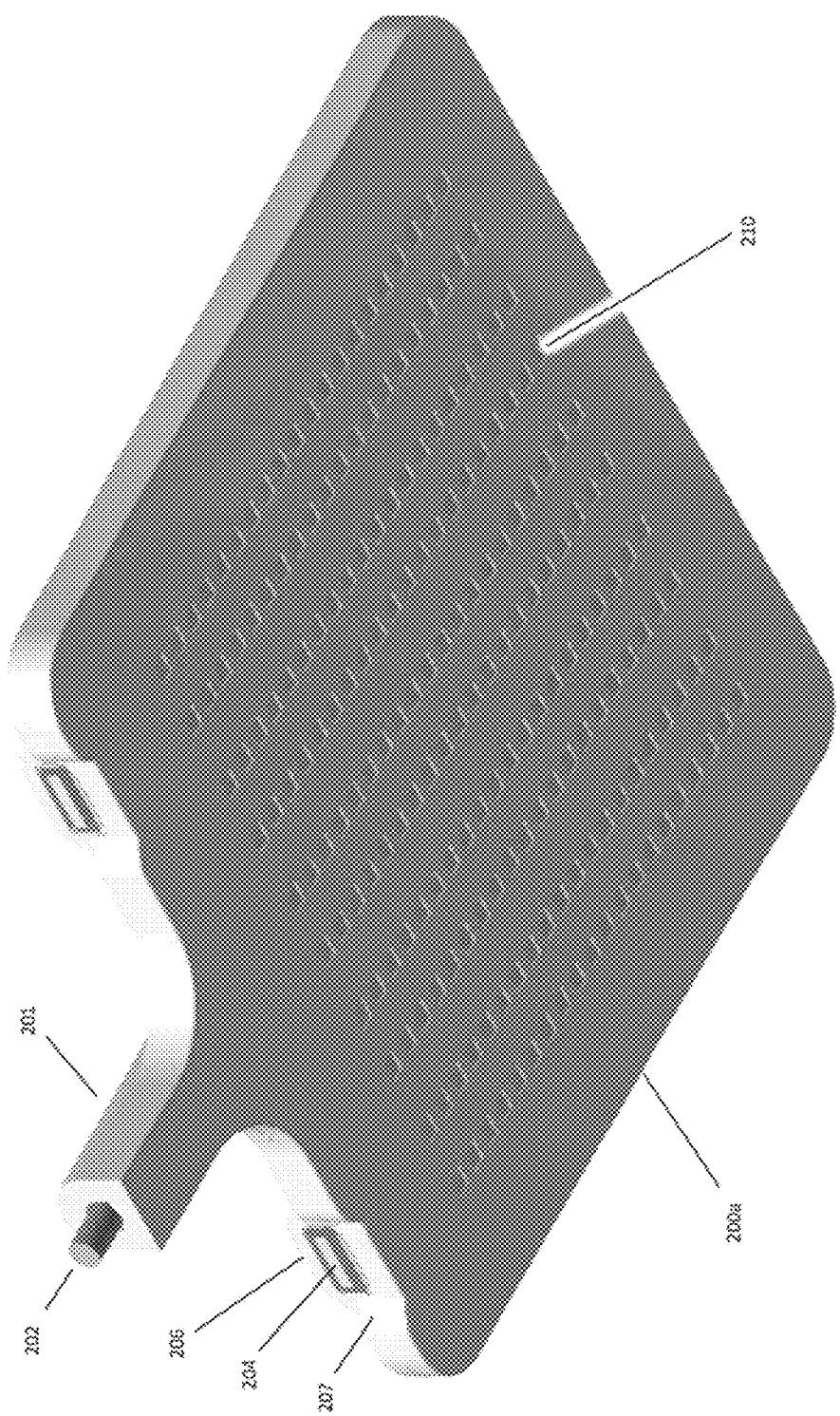

FLEXIBLE LED LIGHT PAD FOR PHOTOTHERAPY

FIELD OF THE INVENTION

This invention relates to apparatus and manufacturing method for phototherapy.

BACKGROUND OF THE INVENTION

Biophotonics is the biomedical field relating to the electronic control of photons, i.e. light, and its interaction with living cells and tissue. Biophotonics includes surgery, imaging, biometrics, disease detection, and phototherapy. Phototherapy is the controlled application of light photons, typically infrared, visible and ultraviolet light, for medically therapeutic purposes including combating injury, disease, and immune system distress.

FIG. 1 illustrates elements of a phototherapy system including an LED driver 1 controlling and driving LEDs as a source of photons 3 emanated from LED pad 2 on tissue 4 for a patient 5. Although the patient 5 is represented by a human brain, any organ or tissue may be treated using phototherapy. Before and after, or during treatment, a doctor or clinician 7 may adjust the treatment by controlling the settings of LED driver 1 in accordance with observations from a monitor 6.

While there are many potential mechanisms, as shown in FIG. 2, the dominant photobiological process 22 responsible for phototherapy occurs within mitochondria 21, an organelle present in every eukaryotic cell 20 comprising both plants and animals including mammals, horses, and humans. To the present understanding, photobiological process 22 involves photon 23 impinging, among others, molecule cytochrome-c oxidase 24, represented symbolically as CCO, which acts as a battery charger increasing the cellular energy content by transforming adenosine monophosphate (AMP) into a higher energy molecule adenosine diphosphate (ADP), and converting ADP into an even higher energy molecule adenosine triphosphate (ATP), in the process of increasing, stored energy in the AMP to ADP to ATP charging sequence 25, cytochrome-c oxidase 24 acts in the manner of a battery charger, with ATP 26 acting as a cellular battery storing energy, a process which could be considered animal "photosynthesis". Cytochrome-c oxidase 24 is also capable of converting energy from glucose resulting from digestion of food to fuel the in the ATP charging, sequence 25, or through a combination of digestion and photosynthesis.

To power cellular metabolism, ATP 26 is able to release energy 29 through a ATP to ADP to AMP discharging process 28. Energy 29 is then used to drive protein synthesis including the formation of catalysts, enzymes, DNA polymerase, and other biomolecules.

Another aspect of photobiological process 22 is that cytochrome-c oxidase 24 is a scavenger for NO 27, i.e. nitric oxide, an important signaling molecule in neuron communication and angiogenesis, the growth of new arteries and capillaries. Illumination of cytochrome-c oxidase 24 in cells treated during phototherapy releases NO 27 in the vicinity of injured or infected tissue, increasing blood flow and oxygen delivery to the treated tissue, accelerating healing, tissue repair, and immune response.

To perform phototherapy and stimulate cytochrome-c oxidase 24 to absorb energy from a photon 23, the intervening tissue between the light source and the tissue absorbing light cannot block or absorb the light. The electromagnetic radiation (EMR) molecular absorption spectrum of human tissue is illustrated in a graph 40 of absorption coefficient versus the wavelength of electromagnetic radiation λ (measured in nm) as shown in FIG. 3. As illustrated, the absorption spectra of deoxygenated hemoglobin shown by curve 44b and also the absorption spectra of oxygenated hemoglobin shown by curve 44a, i.e. blood, strongly absorb light in the red portion of the visible spectrum, especially for wavelengths shorter than 650 nm. At longer wavelengths in the infrared portion of the spectrum, i.e. above 950 nm, EMR is absorbed by water, i.e. by $H_2O$, as shown by the absorption spectra of curve 42 and to a lesser degree by the absorption of lipids and fats shown by curve 43. In between 650 nm to 950 nm, human tissue is essentially transparent as illustrated by transparent optical window 45.

Aside from absorption by fats and lipids shown by curve 43, EMR comprising photons 23 of wavelengths λ within in transparent optical window 45, are directly absorbed by cytochrome-c oxidase as shown by the absorption spectra of curves 41a and 41b. Specifically, the 41b portion of the absorption spectra of cytochrome-c oxidase 24 is absorbed by infrared red unimpeded by water or blood. A secondary absorption tail for cytochrome-c oxidase shown by curve 42a illuminated by light in the red portion of the visible spectrum is partially blocked by the absorption properties of deoxygenated hemoglobin shown by curve 44b, limiting any photobiological response for deep tissue but still activated in epithelial tissue and cells. In this regard, phototherapy for skin and internal organs and tissue requires different treatments and light wavelengths, red for skin and infrared for internal tissue and organs.

Importance of Photonic Delivery System

In any case, to achieve maximum energy coupling into tissue during phototherapy, it is important to devise a consistent delivery system for illuminating tissue with photons consistently and uniformly. While early attempts used filtered lamps, lamps are extremely hot and uncomfortable for patients, potentially can burn patients and doctors, and are extremely difficult in maintaining uniform illumination during a treatment of extended duration. Lamps also suffer short lifetimes, and if constructed using rarified gasses, can also be expensive to replace regularly. Because of the filters, the lamps must be run very hot to achieve the required photon flux to achieve an efficient therapy in reasonable treatment durations. Unfiltered lamps, like the sun, actually deliver too broad a spectrum and limit the efficacy of the photons by simultaneously stimulating both beneficial and unwanted chemical reactions, some involving harmful rays, especially in the ultraviolet portion of the electromagnetic spectrum.

As an alternative, lasers were later used to perform phototherapy. Like lamps, lasers risk burning a patient, not through heat, by exposing tissue to intense concentrated optical power. To prevent that problem, special care must be taken that laser light is limited in its power output and that unduly high current producing dangerous light levels cannot accidentally occur. A second problem derives from a laser's small "spot size", the illuminated area. Because a laser illuminates a small focused area it is difficult to treat large organs, muscles, or tissue and it is much easier for an overpower condition to arise. Another consideration of laser light is its "coherence" the property of light preventing it from spreading out, making it more difficult to cover large areas during treatment. Studies also reveal there is no inherent extra benefit from phototherapy using coherent light. For one thing, life evolved on scattered, not coherent light. Secondly, the first two layers of epithelial tissue already destroys any optical coherence, so the presence of coherence is really relegated to light delivery but not to its absorption.

Moreover, the optical spectrum of a laser is too narrow to fully excite all the beneficial chemical and molecular transitions needed to achieve high efficacy phototherapy. The limited spectra of a laser, typically a range of ±3 nm around the laser's center wavelength value, make it difficult to properly excite all the beneficial chemical reactions needed in phototherapy. For example, referring again to FIG. 3, clearly the chemical reactions involved in making the CCO absorption spectra 41b is clearly different than the reactions giving rise to absorption tail 41a.

So just as sunlight has an excessively broad spectrum, photobiologically exciting many competing chemical reactions with many EMR wavelengths, some even harmful, laser light is too narrow and does not stimulate enough chemical reactions to reach full efficacy in phototherapeutic treatment. This subject is discussed in detail a related application entitled "Phototherapy System and Process Including Dynamic LED Driver with Programmable Waveform", by Williams et. al. (U.S. patent application Ser. No. 14/073,371), incorporated herein by reference.

To deliver phototherapy by exciting the entire range of transparent optical window 45, i.e. the full 300 nm width, then even if four different wavelength light sources were employed to span the range, each light source would require a bandwidth almost 80 nm wide, more than an order of magnitude wider than that of a laser light source. This range is simply too wide for lasers to cover.

In contrast, today's commercially available light-emitting diodes (LEDs) are capable of emitting a wide range of light spectra from the deep infrared through the ultraviolet portion of the electromagnetic spectrum. To be effective therapeutically, however, the LEDs must be stably positioned atop the area to be treated. In FIG. 4A, for example, an LED wand or hairbrush 60 comprising a stiff array of LEDs suffers numerous issues, severely diminishing its utility and relegating its use to that of a toy. Its first issue is a matter of "fluence", the total quantity of photons delivered by a phototherapy system during a treatment. Phototherapy treatments run between 20 minutes to over an hour and may involve several treatments in sequence. Since it takes time for cells to begin to react to biophotonic stimulation, applying a treatment for only a few minutes accomplishes nothing. But practically speaking, it is uncomfortable or nearly impossible to hold a handheld wand in one position for an hour or more.

The importance of maintaining the LED array in a constant position above tissue being treated is highlighted in the graphics of FIG. 4A, depicting an LED wand 60 being held at various distances above a treated array comprising epithelial layer 61 and subdermal tissue 62. In the leftmost case, where the LED wand 60 is held high above the treatment area, the light expands to cover a large area but only penetrates into the skin at a shallow depth 63, barely reaching subdermal tissue 62 where healing occurs. In the center case, LED wand 60 is held at an intermediate distance whereby the light spreads out less, covering a smaller area but penetrating into the tissue to a greater depth 64. In the rightmost case, LED wand 60 is held against epithelial layer 61 and penetrates deeply into subdermal tissue 62 to a greater depth 65 but with a much smaller area than that of the leftmost case shown. By moving the wand, an unavoidable condition in any real treatment, any and all of the cases shown may occur. Each time the epidermal tissue being treated changes by moving the placement of LED wand 60 the treated area and depth changes, essentially restarting the treatment.

The arrangement shown in FIG. 4B, which includes a stiff LED panel 66 that is strapped onto a patient is better in the sense that the LEDs are held firmly in place, but it still suffers from variable penetration depth because most human or animal appendages are treatment areas are not flat, but are curved. A stiff LED panel 66 cannot bend to adapt to the curves of a patient's body. The effect is that the light's penetration depth 67 in the center of the area being treated is much greater than the penetration depth 68 located under the edge of the panel 66 because it does not curve of flex to it the body.

FIG. 4C illustrates that the best solution to the light delivery problem is to employ a flexible LED pad, one that curves to a patient's body. As shown, flexible LED pad 70 may be bent to fit a body appendage.

The resulting benefit, shown in FIG. 4C illustrates that the resulting light penetration depth 76 into subdermal tissue 62 from the LEDs 72 comprised within flexible pad 70 is perfectly uniform along the lateral extent of the tissue being treated. Unlike the previous examples, where the light source as a stiff LED wand or inflexible LED panel are held above the tissue being treated, in this example the flexible LED pad 70 comes in contact with the patient's skin, i.e. epithelial 61. To prevent inadvertent spread of virulent agents through contact to LED pad 70, a disposable aseptic barrier 71, typically a clear plastic layer is inserted between light pad 70 and the patient.

To enable it to bend into various shapes, light pad 70 comprises a flexible polymeric material. Likewise, printed circuit board 71, to which LEDs 72 and integrated circuit package 74 are attached, may also comprise a flex PCB (printed circuit board) material. In such cases however, if the flex PCB 73 bends and LEDs 72 or integrated circuit package 74 do not, stress will be placed on any leads 75 used to attach the electronic component to flex PCB 73. Repeated stress can lead to stress fractures, poor reliability, and even open circuits.

Another consideration is manufacturing of the LED pads. If the flexible polymeric material is porous, chemically or biologically reactive, it can harbor viruses or bacteria in its surface cavities, infecting subsequent users, or retain harmful fluids, acids or toxins on its surface potentially harming the next patient to employ the LED pad. LED pads are often used in non-aseptic environments and may be applied onto infected or broken skin, e.g. over a cut or an acne pimple. If the polymeric pad is porous or is not inert and hypoallergenic, its repeated use may result in adverse reactions or cross-contamination among patients. The pad's polymeric material must also be compatible with regular alcohol or disinfectant cleanings needed to insure an aseptic contagion-free surface without degrading the polymer or impacting the LED pad's electrical function. Ideally it should also be compatible with disinfection in a UV or ozone disinfection chamber.

A complete phototherapy system for controlled light delivery available today, shown in the pictograph of FIG. 5, comprises an electronic driver 90 connected to one or more sets of flexible LED pads 91a-91e through cables 91a and 91b and connected to one other through short electrical connectors 93a-93d.

Specifically, one electrical output of electronic driver 90 is connected to a center flexible LED pad 91a by an electrical cable 92a which is in to connected to associated side flexible LED pads 91b and 91c through electrical connectors 93a and 93b respectively. A second set of LEDs pads connected to a second electrical output of electronic driver 90 is connected to center flexible LED pad 91c by electrical cable 92b which is in turn connected to associated side flexible LED pads 91d and 91e through electrical connectors 93c and 93d respectively located on the edges perpendicular to the edge where electrical cables 92a and 92b attach.

FIG. 6 illustrates a schematic representation of the light delivery system comprising a set of three flexible LED pads with center flexible LED pad 105a and side flexible LED pads 105b and 105c. The center flexible LED pad 105a is identified by its integrated electrical cable 100 used to connect the LED pad to the electronic driver, including a plug 101 and a hardwired pad-to-cable connection 102. Center flexible LED pad 105a in turn connects to side flexible LED pads 105b and 105c (collectively as flexible LED pads 105) through short electrical connectors 103a and 103b, plugging into corresponding sockets 104, with two such sockets located on the edges of every flexible LED pads. On the center pad 105a these sockets 104 are located on the pad's edges perpendicular to the edge where electrical cable 102 attaches.

In this example, sockets 104 are located at the edge facing one another and interconnected electrically by straight electrical connector 103a and 103b. In other implementations the connectors face one another and are located in the center edge of the pads, as shown in FIG. 5. In a similar manner, the connectors face one another and are interconnected by straight electrical connectors 93a and 93b. Because the sockets face one another the straight electrical connectors must be made short in order to afford the opportunity to position the flexible LED pads close to one another. In therapeutic treatments, the flexible LED pads are held tightly in place by a Velcro belt 107 laid across the back of the pads oriented parallel to electrical connectors 103a and 103b and perpendicular to hardwired center pad-to-cable connection 102. Optional Velcro straps 108 may be glued to the flexible LED pads 105, except in practice it is easy to dislocate, literally rip, the Velcro straps 108 away from the flexible LED pads 105, in part because of the biologically inert material needed in their manufacture. If the lengths of straight electrical connectors 103a and 103b are made too long, or Velcro strap 107 is pulled too tightly, undue stress on the electrical connectors may result, resulting in wires torn from the connector plug, broken wires, or broken plugs, generally resulting in an open circuit.

Reliability Issues with Flexible LED Pads

While the need for flexible LED pads forms the basis of delivering consistent phototherapy to patient's skin and organs for extended durations, the pad's very flexibility is a fundamental source of reliability problems with their practical implementation.

For example, as an LED pad is used repeatedly, including being twisted, bent, curved, laid upon, and otherwise shaped to fit the contours of a patient's body, the repeated bending of the LED pad tends to move the PCB (or PCPs) contained within the LED pad till eventually many of the LEDs do not line up with the holes in the pad. For example, as shown in pictograph 120a of FIG. 7, LED pad 105a includes an array of openings 106 aligned to the LEDs emitting photons. A close-up of area 121 shown in pictograph 120b illustrates that while some LEDs 122 are properly aligned to the openings in pad 105a, others are laterally displaced like misplaced LED 123 covering part or all of the LED and blocking any light from being administered to a patient being treated.

Another issue, shown in FIG. 8, is that repeatedly bending a flex PCB may result in cracking of solder connecting component leads to the PCB. For example, in pictograph 125a LED 122 mounted onto PCB 123 exhibits after repeated use an electrical connection problem at solder connection 124c, shown in expanded detail 125b, were an electrical open circuit occurred as a result of crack 126 separating the LED's electrical connection, a copper lead, from the PCB conductive trace, resulting in an electrical failure in the LED pad.

FIG. 9 illustrates another problem resulting from repeated bending and handling of the flexible LED pad. In this case the electrical cable connecting the center flexible LED pad to the electronic driver experienced a failure in its hardwired pad-to-cable connection 102 where without sufficient strain relief, pulling on the cable dislodged the connector from the wire terminator 132 and created an electrical open circuit between electrical cable 102 and the pins 131 connected to the PCB resulting in a non-functional LED pad.

Similar failures occurred in the pad-to-pad electrical connectors 103 as shown in FIG. 10, where after repeated use cable 103b pulled out of plug 135 at failure point 136 to cause an electrical open circuit. Such failures can occur if the lengths of straight electrical connectors 103a and 103b exemplified in FIG. 6 are made too long, or Velcro strap 107 is pulled too tightly, resulting in undue stress on the electrical connectors whereby the wires may be broken or torn from the connector plug, resulting in an open circuit.

In the prior art design, then, broken wires, solder joints and leads are problematic, especially because the flexible LED pads are routinely stretched, bent, compressed and adjusted during treatments. Even in the case of attempts to use multiple stiff PCBs 140a, 140b, and 140c connected by jumper wires 141a and 141b within a flexible LED pad as shown in FIG. 11, repeated bending of the flexible LED pad eventually results in illustrated failure 142, where the wire jumper suffers an open circuit to the PCB conductive trace, breaking, the wire at the point of the solder joint. This observation is comparable to that of automotive manufacturers who claim that every discrete wire connected to an external rear view mirror costs million of dollars in replacement costs from wire breakage. As a result, eliminating and minimizing those wires is today a best practice in the automotive industry.

Another issue affecting consistent performance of any network of flexible LED pads is one of voltage drop in the wires and connectors resulting from electrical resistance. Using voltage control, the current in a particular series string of LEDs depends on the power supply voltage $+V_{LED}$ and the total series resistance between the particular string $R_{series}$. Because the total series resistance is sensitive to the resistance within the flexible LED pads, the brightness of the LED string may not be uniform, depending on PCB manufacturing and the interconnection of the flexible LED pads by the user.

For example, FIG. 12A represents a simplified schematic drawing of a voltage driven LED phototherapy system comprising a LED controller unit 90 driving a set of three flexible LED pads 105a, 105b and 105c. As shown, LED pad 105a, the one with cable 100 connecting the pad to LED controller 90 through connector 101, is electrically located in the center between the other two LED pads 105b and 105c and supplies power to both LED pads 105b and 105c. This electrical configuration, one with a center pad connected to a power supply feeding power directly to two side pads, is for clarity sake referred to herein as a "T" configuration for connecting the LED pads. Within LED controller unit 90 is a controlled voltage source 150 that supplies a voltage $+V_{LED}$ whenever it is on and 0 volts when it is off. The supply may be turned on continuously or pulsed during an actual phototherapy treatment.

Within each flexible LED pad is an array of LEDs connected in a combination of series strings which themselves are connected in parallel. For clarity, most of the LEDs have been intentionally been omitted in FIG. 12A and FIG. 12C, where only the center and edge LED strings are shown. For example, for the pad 105a, i.e. one connected directly to LED controller 90, only center LED string 156a and edge strings 155a and 157a are illustrated. Any number of additional LED strings may be included between the LED strings shown. A similar arrangement exists for flexible LED pads 105b and 105c. Each LED string, depicted as single LEDs 155a, 156a, and 157a actually comprise a series circuit comprising a number of LEDs, from 1 to 40, and a bias resistor despite the fact that only a single LED is shown.

For clarification of terminology, note the term "center" pad is sometimes used to identify LED pad 105a as a pad with connected cable 100 and to distinguish it from other LED pads lacking connected cables regardless of the pads are topologically interconnected. The presumption that any LED pad with a connected cable is by definition the "center" pad as shown by pad 105a in the T-shaped electrical topology shown in FIG. 12A, is in recognition that electrically configuring the pads in an L-shaped circuit topology as shown in FIG. 12C with pad 105a on the end, is electrically inferior because the current must flow through a longer path with greater series resistance.

An example of the equivalent circuit of LED 156a is shown in FIG. 12B comprising series-connected LEDs 158a, a series of in LEDs 1 through m as shown, and bias resistor 159a. The bias resistor 159a may range from 1 ohm to several hundred ohms, but it cannot be so high in value as to prevent the required current from flowing. The current $I_{LED}$ through each string can be calculated with the following equation:

$$I_{LED}=(V_{bias}-m \cdot V_f)/R_{bias}$$

wherein $V_{bias}$ is the voltage applied across the serial combination of LED string 158a and bias resistor 159a, m is the number of series-connected LEDs in the LED string 158a, $V_f$ is the average forward voltage drop of each of the LEDs 1 through m in LED string 158a during conduction, and $R_{bias}$ is the resistance of bias resistor 159a. For example, if $V_{bias}$=30V, m=20, and $V_f$=1.4V, and $R_{bias}$=67Ω then $(V_{bias}-m \cdot V_f)$=2V and $I_{LED}$=30 mA.

Returning to FIG. 12A, each flexible LED pad contains parasitic resistance associated with the PCB conductive traces depicted as resistors 151a, 152a, 153a an 154a in flexible LED pad 105a and similarly in the other LED pads. Ideally these parasitic resistances are zero and the only resistance present in the LED pad is the discrete $R_{bias}$ resistor used to set the LED currents. In such a case no voltage drop occurs across the conductive traces and the entire supply voltage is biased across each and every LED string, i.e. where $+V_{LED}=V_{bias}$. In prior art flexible LED pads, however, the PCB conductive traces have resistance and exhibit a voltage drop, red the $V_{bias}$ voltage on each LED string and affecting the LED brightness. The problem of parasitic resistance is further exaggerated in the case of flexible PCBs, which naturally employ thinner conductive traces in order to maintain flexibility.

If all the voltage drops resulting, from parasitic resistance were uniform, the LEDs would be uniformly less bright, and the problem could be adjusted simply by changing the value of the supply voltage $+V_{LED}$ or the bias resistors $R_{bias}$ to correct for the effect of the parasitic resistance. The problem however, is that the effect of the parasitic resistance is not uniform and in fact, depends on the PCB layout and even on the way the LED pads are connected. For example, in the T configuration shown in FIG. 12A, the center pad 105a supplies power to the side pads 105b and 105c in the shortest possible path, meaning power entering flexible LED pad 105a through cable 100 is delivered to connector 103a and flexible LED pad 105b through only two resistors 152a and 154a, and does not flow through flexible LED pad 105c. Similarly, power entering flexible LED pad 105a through cable 100 is also delivered to connector 103b and flexible LED pad 105c through only two resistors 151a and 153a, and does not flow through flexible LED pad 105b.

Even though in the T configuration power does not flow through multiple pads, resistance within a pad results in a gradation of voltage across the LED array within a pad. For example, power is delivered to LED string 155b in flexible LED pad 105b through only two parasitic resistors 152a and 154a, but power to LED string 157b is conducted through six parasitic resistors, namely 152a, 151b, 152b, 154b, 153b, and 154a, a factor of three higher parasitic resistance. The problem of distributed parasitic resistance is manageable within a single pad because the current within a given pad is limited to a maximum of $n \cdot I_{LED}$, where "n" is the number of LED strings in a given LED pad and $I_{LED}$ is the current flowing through each string of LEDs. For example, in the T configuration shown in FIG. 12A, the total current flowing through connectors 103a and into flexible LED pad 105b assuming n=10 and $I_{LED}$=30 mA is only 300 mA in total.

If however, the flexible LED pads are configured in an "L" shaped configuration shown in FIG. 12C where the power supply connected flexible LED pad 105a is connected at the end of a set of three interconnected LED pads, the parasitic resistance problem is significantly worse. Consider the series parasitic resistance of the circuit driving the farthest LED string 155b in the circuit, comprising 10 parasitic resistors 151a, 152c, 151c, 152b, 151b, 153b, 154b, 153c, 154c, and 153a. The L configuration results in 67% more parasitic resistance, i.e. 10/6 times, than the same LED pads connected in at T configuration. The user may then experience a diminished brightness in flexible LED pad 105b, the last LED pad in the chain. Moreover, the PCB traces in flexible pad 105c connected to connector 103b must carry all the current for both flexible LED pads 105c and 105b, i.e. a total of 600 mA. In prior art flexible LED pads, the performance and even LED pad reliability suffer whenever users connect the LED pads in the L configuration. While user instructions advise the LED pads should not be connected in the L configuration, for applying treatment from the base of the neck and down the spine it is inconvenient to use the T configuration unless the patient removes their shirt or blouse.

Another consideration in flexible pad design, including cabling, is that of electrical noise and electromagnetic compatibility, or EMC. Since the total current being pulsed on and off in a set of three pads can exceed 900 mA and may be modulated at 20 kHz frequencies or greater, shielding and noise management is an important consideration, especially in order to pass FCC class-B certification needed for medical devices. Inadequate shielding can result is several issues, including false turn on of LEDs. For example, without proper shielding, driving a LED pad comprising both red and infrared LEDs can result in the red LEDs being slightly illuminated when only the infrared LEDs are being pulsed, a consequence of capacitive coupling between control lines used to turn the separate LED strings on and off. For example, in the pictograph of FIG. 13, a flexible LED pad 105a comprises both red and infrared LEDs. A special electronic camera 170 is able to "see" both infrared and red light and to display the camera images of both visible and infrared light on an LCD display with visible light. Even though only the infrared LEDs should be illuminated in the example shown, if flexible LED pad 105a is operated by pulsing the infrared LEDs on and off while maintaining the red LEDs in an off condition, both the infrared. LEDs and the red LEDs simultaneously conduct and both generate light. The magnitude of the problem increases in proportion to the modulating frequency of the infrared LEDs, indicating the noise coupling is capacitive (because the impedance of a capacitor and hence the noise coupling decreases with increasing frequency). The greater the magnitude of capacitive coupling, the more pronounced the noise coupling effect, meaning longer cables exhibit greater noise sensitivity than shorter cables. Short cables, however, limit physicians in their ability to comfortably perform treatments on customers in crowded clinic rooms. In the gray-scale drawing of FIG. 13, the illuminated LEDs on the pad 105a correspond to the bright images 172 on the screen of camera 170, the only LEDs that should be illuminated. But as illustrated, the dim images 171 on the screen of camera 170 reveal off state LEDs, LEDs that should not emit light or be present in the LCD image, are in fact emitting light. Light emission from LEDs biased into and off condition represents a malfunction.

So in the present generation of flexible LED pads, the use of flex PCBs results in broken solder connections between component leads and the flex PCBs, while the used of stiff PCBs results in broken wire and broken solder joints where the jumper wires connect to the PCB conductive traces. Either way, the result is a broken conductive path and intermittent operation or permanent disabling of the LED pad's operation. For these and many other reasons, the majority of the product offerings in phototherapy today utilize hard, stiff and inflexible pads—pads that do not contour to a patient's body and appendages, and therefore do not uniformly administer phototherapeutic treatment in a consistent or beneficial manner, sacrificing treatment efficacy for product reliability. Flexible LED pads sold to consumers, break and malfunction easily, and are not designed to work reliably after repeated use, especially in their professional application as used by doctors, therapists and clinics for humans or for animals.

What is needed is a new design for, and a means to manufacture flexible LED pads for phototherapy that do not suffer the aforementioned reliability and performance failures caused by improperly positioned or dislocated LEDs; broken connectors, wires, and solder joints; parasitic resistance; and noise.

SUMMARY OF THE INVENTION

According to this invention, the PCBs in a flexible LED pad are linked together by means of ribbon cables which mate with corresponding electrical connectors firmly mounted on the PCBs. Hence, there are no solder connections to wires in the electrical paths linking one PCB to another PCB, and the above-mentioned risk of breakage from bending or other manipulation of the LED pads or their interconnections during treatment is eliminated. Similarly, in one embodiment the control cable linking one or more of the flexible LED pads to an LED control unit terminates at an electrical connector on one of the flexible LED pads, likewise eliminating the risk of solder joint breakage as the flexible LED pads are moved about in the course of a phototherapy treatment. In another embodiment, the LED pad comprises a strain relief that includes a feature, e.g., a notch, which mates with a corresponding feature on the cable to prevent breakage where the wires in the cable are attached to the LED pad. The cable linking the LED pad and the LED control unit is preferably shielded.

The electrical connectors mounted on the PCBs may comprise low-profile socket connectors that mate with plugs on the ribbon cables, although other types of male or female connectors may be used to connect the ribbon cables to the PCBs. In one embodiment, the electrical connector linking the flexible LED pad to the LED control unit is a USB socket connector and the cable connecting the LED pad to the control unit comprises a RJ45-to-USB adapter which connects to a RJ45 socket on the control unit. The invention, however, is not limited to any particular type of electrical connector, male or female.

The PCBs and other internal components of the flexible LED pad are enclosed in a flexible, e.g. polymeric, material which includes a top piece and bottom piece that are glued together. Openings in the bottom piece are aligned with LEDs mounted to the PCBs. To ensure that the LEDs do not come out of alignment with the openings as the LED pad is bent or otherwise manipulated during a phototherapy treatment, the PCBs are fitted snugly into recesses or "downsets" in the bottom piece, and posts from the bottom piece protrude through openings in the PCBs, further anchoring the PCB in the bottom piece and prevent misalignment between the LEDs and openings in the bottom piece.

A group of flexible LED pads may be linked together in a chain that can be, for example, wrapped around an arm or leg of a patient undergoing phototherapy treatment. The LED pads may be physically linked together by means of Velcro tape that is attached to each pad and a Velcro strap that is fastened to the Velcro tape on each LED pad. The Velcro tape is attached to the relatively inert flexible material of the pad by means of an adhesive film which is attached to the pad by means of a first adhesive material and to the Velcro tape by means of a second adhesive material. In one embodiment, the flexible LED pad comprises an inert nonporous polymeric material such as Teflon or silicone, the adhesive film comprises a polyester film, the first adhesive material comprises silicone glue or epoxy and the second adhesive material comprises an acrylic-based glue.

The flexible LED pads and the LED control unit may be arranged in a T configuration, wherein the control unit is connected directly to a central LED pad in the chain, or in an L configuration, wherein the control unit is connected directly to an LED pad at an end of the chain.

Further details of the invention will become apparent to those of skill in the art by reference to the following drawings and written description of the invention.

BRIEF DESCRIPTION OF THE DRAWINGS

In the drawings listed below, components that are generally similar are given like reference numerals.

FIG. 21A is a view of the disclosed flexible LED pad comprising, a center pad with integrated connecting cable, two side pads, and two unplugged pad-to-pad connectors.

FIG. 22 is an underside perspective view of the center pad of the disclosed flexible LED pads including an integrated connector cable.

FIG. 29 is a top perspective view of the center pad of an alternative embodiment of the disclosed flexible LED pads illustrating the top and bottom assemblages including PCBs contained within.

DESCRIPTION OF THE INVENTION

Figure 1:
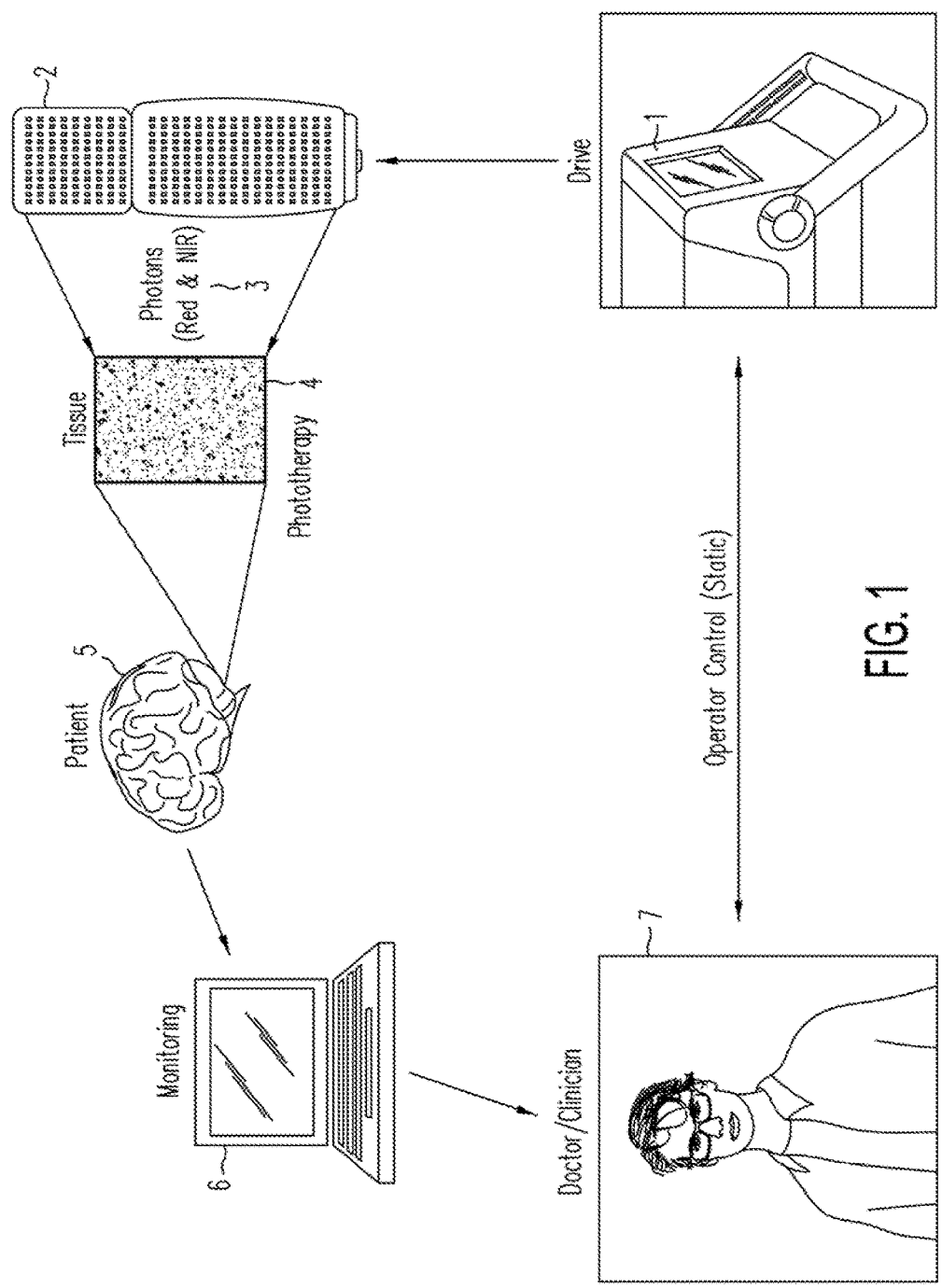
FIG. 1 is a schematic representation of a physician-supervised phototherapy treatment.
Figure 2:
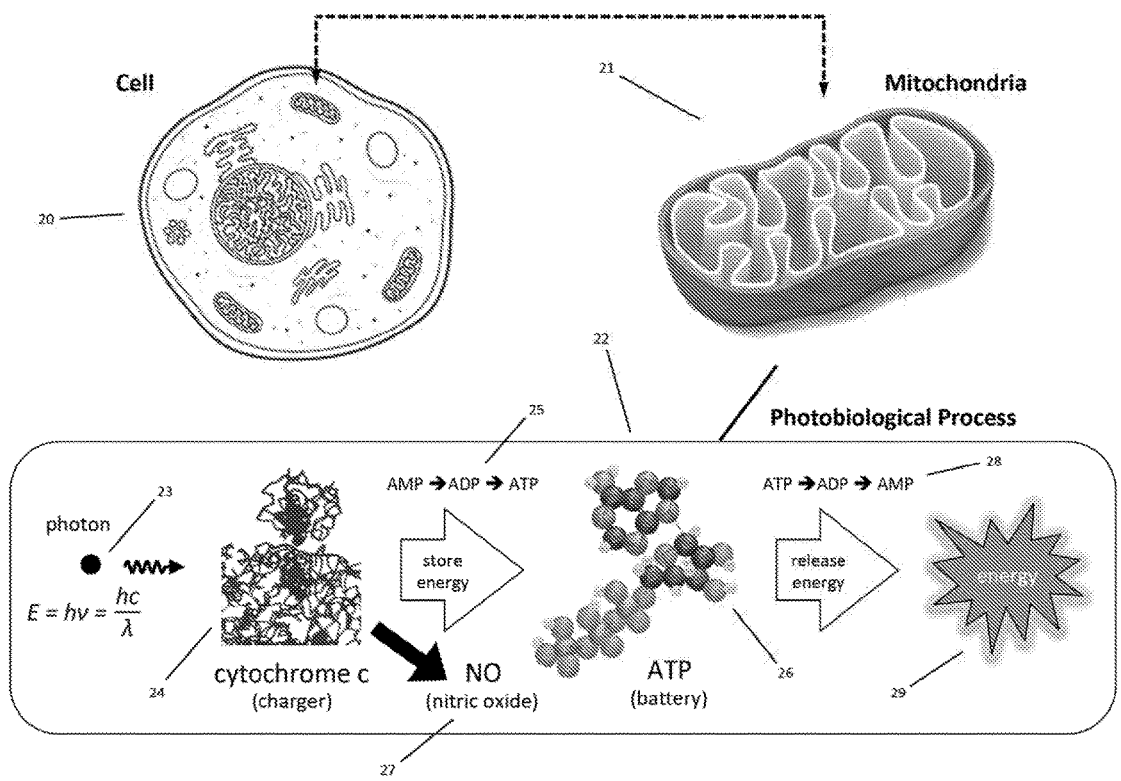
FIG. 2 is a schematic representation of a known photobiological process resulting from phototherapy.
Figure 3:
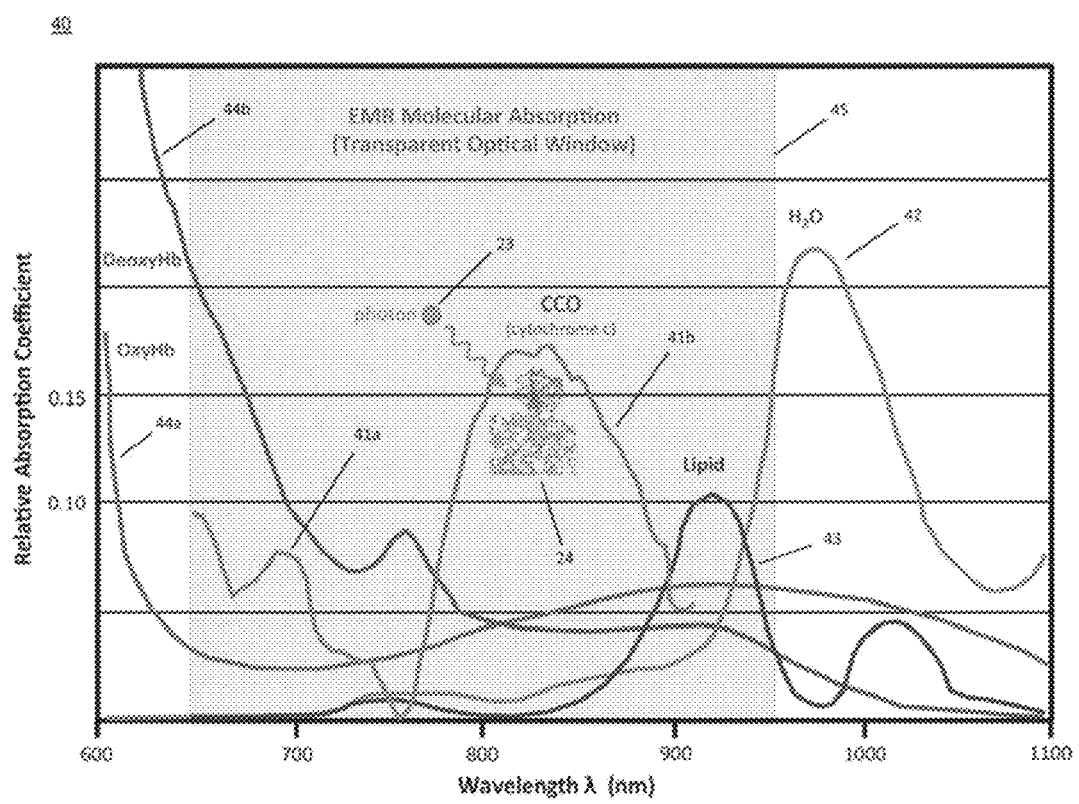
FIG. 3 is a graph showing the absorption spectra of EMIR for different types of human tissue.

In order to facilitate reliable yet flexible LED pads for phototherapy that do not suffer the aforementioned reliability and performance failures caused by dislocated LEDs, broken connectors and wires, parasitic resistance, and noise, an entirely new design and manufacturing methodology must be adopted, one previously unused in phototherapy apparatus or manufacturing.

The design concept includes the principle of eliminating most if not all wire interconnections, and when flexible interconnections are employed, to eliminate stress on individual wires by employing integrated strain relief into the polymeric mold, by utilizing multi-conductor cable (such as ribbon cable) with low-profile socket-plug connectors for interconnections within a flexible LED pad, and by utilizing robust pre-molded cable and industry-proven socket-plug connectors (like USB cables) for interconnections among the LED pads and between the pads and the LED controller. By redesigning the flexible LED pad design to change the orientation of electrical connectors perpendicular to that of the pad's mechanical support, unnecessary wire stress is also eliminated. Moreover, internal to the flexible LED pad's construction, segmented rigid PCBs are interconnected, through low profile ribbon cables using, a plug-socket connection arrangement to relieve wire stress during flexing and bending of the LED pad occurring in normal use.

A ribbon cable (also known as multi-wire planar cable) is a cable with many conducting wires running parallel to each other on the same flat plane. As a result the cable is wide and flat resembling its namesake, a piece of ribbon. The main point of ribbon cables is to allow mass termination to specially designed connectors in which the ribbon cable is forced onto a row of sharp forked contacts present in a multi-pin "plug" which in turn is plugged into a PCB mounted socket.

Using a plug termination on the end of the ribbon cable and plugging this plug into a socket mounted on the stiff PCB eliminates the need for soldering individual wires to the PCB. As such, the risk an individual wire resulting in a broken solder joint from an accidental wire pull is essentially eliminated. Because multiple pins of the socket are soldered onto the stiff PCB, the socket is firmly mounted and difficult to damage or break. If the ribbon cable is pulled too firmly, the plug will disconnect from the socket rather than tear the wire or break the solder joints. The ribbon cable is chosen to be sufficiently long to accommodate the bending of the pad without applying any force onto the ribbon cable socket. As a result reliability is improved even in LED pads with repeated flexing and bending. All external cables are shielded to manage noise and maintain electromagnetic compatibility consistent with the medical and hospital environment.

Construction of the LED pad's polymeric material comprises silicone or Teflon formed at temperatures sufficiently high to liquefy and inject the polymer into a mold to form its shape and pattern, and upon cooling to form an inert non-porous surface free from cavities capable of harboring virulent agents. The polymer is also medical grade hypoallergenic material, chemically or biologically un-reactive thereby preventing the formation or adhesion of chemical or biological agents that may contaminate, infect, burn, irritate or otherwise harm skin. The pad's polymeric material is non-reactive, compatible with regular alcohol or disinfectant cleanings needed to insure an aseptic contagion-free surface without degrading the polymer or impacting the LED pad's electrical function. It is also compatible with disinfection in a UV or ozone disinfection chamber.

Improved Flexible LED Pad Design

Figure 14A:
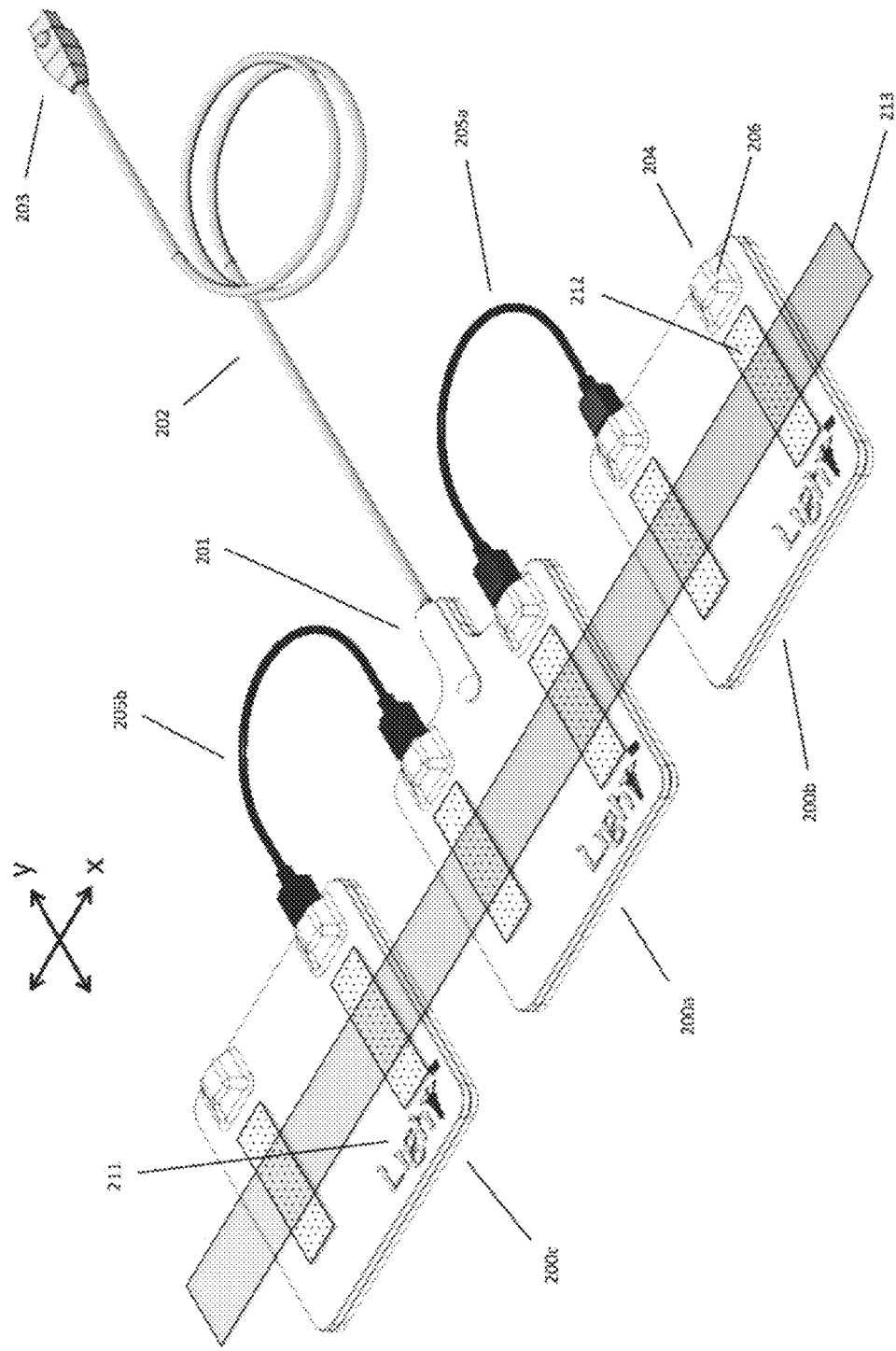
FIGS. 14A and 14B are views of the disclosed flexible LED pad comprising a center and two side pads.
Figure 14B:
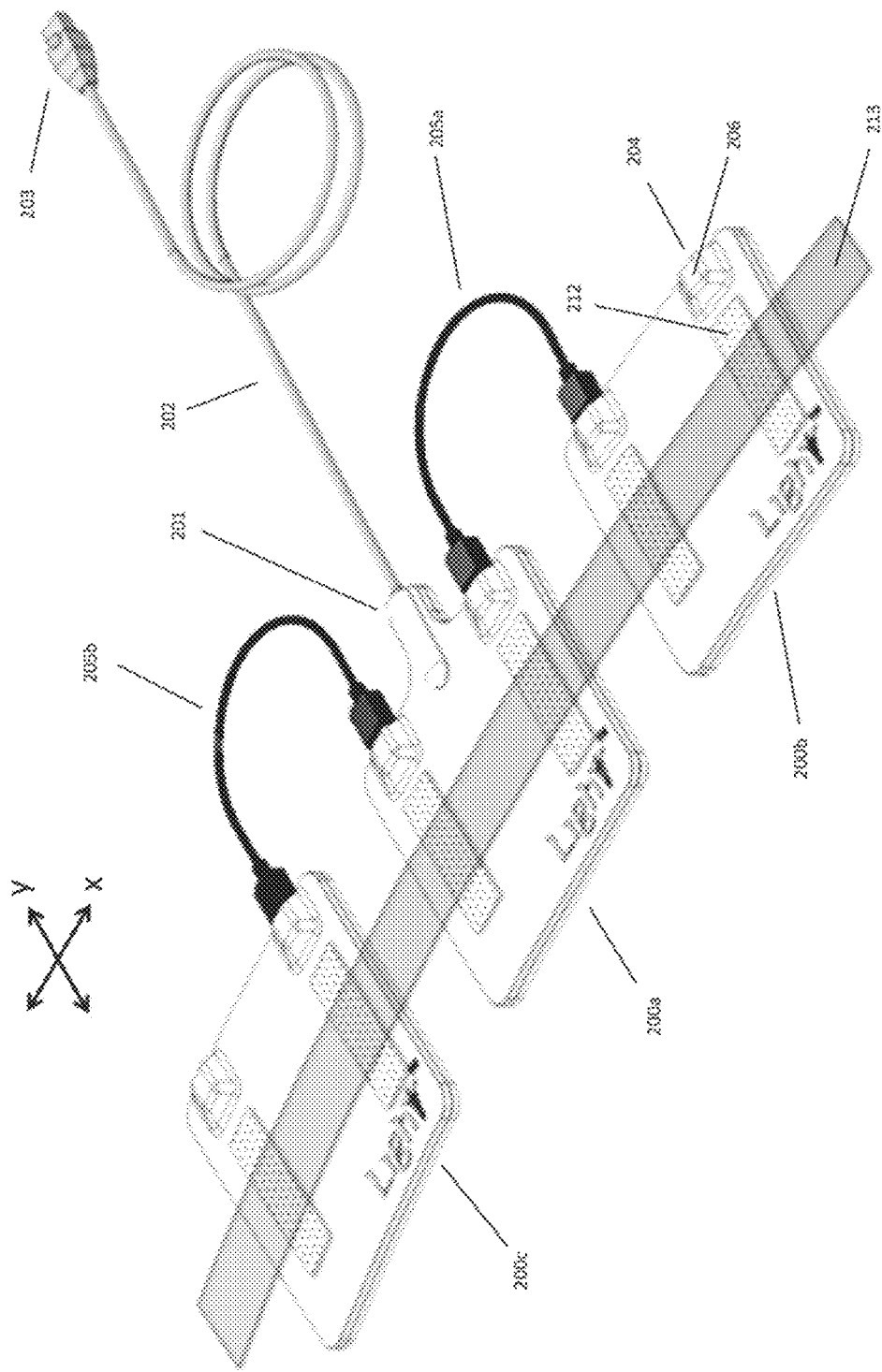

FIG. 14A illustrates a plan view of an inventive flexible LED pad set consistent with the aforementioned goals and design principles, which aside from electrical cable 202 and its hardwired interconnection into center flexible LED pad 200a, completely eliminates all discrete wires and any wires soldered directly into PCBs while enabling significantly greater flexibility in positioning and arranging the flexible LED pads upon a patient undergoing phototherapy.

As shown, the LED pad set includes three flexible LED pads comprising center flexible LED pad 200a with associated electrical cable 202, and two side flexible LED pads 200b and 200c. All three pads include two connector sockets 204 for connecting pad-to-pad cables 205a and 205b. Although connector socket 204 is not visible in this perspective drawing as shown, its presence is easily identified by the hump 206 in the polymeric flexible LED pad 200b, and similarly in flexible LED pads 200a and 200c. Pad-to-pad cables 205a and 205b electrically connect center LED pad 200a to LED pads 200b and 200c respectively.

While any cable, plug and socket may be utilized for pad-to-pad connections it is advantageous to use a proven industry standard connector system to maintain high performance and consistent quality at competitive costs manufactured through a well-established high-volume supply chain, using sockets that securely mount to a printed circuit board, and using cabling that integrates electrical shielding and molded plus resisting breakage from repeated flexing and bending. Moreover the connector cables should be capable of reliably conducting up to 1 A and avoid excessive voltage drops or electromigration failures during extended use. Connector and cable set options include USB, min-USB, IEEE-1394, and others. In the examples shown, a 8-pin rectangular USB connector format was chosen for its durability, strength, and ubiquity.

Figure 5:
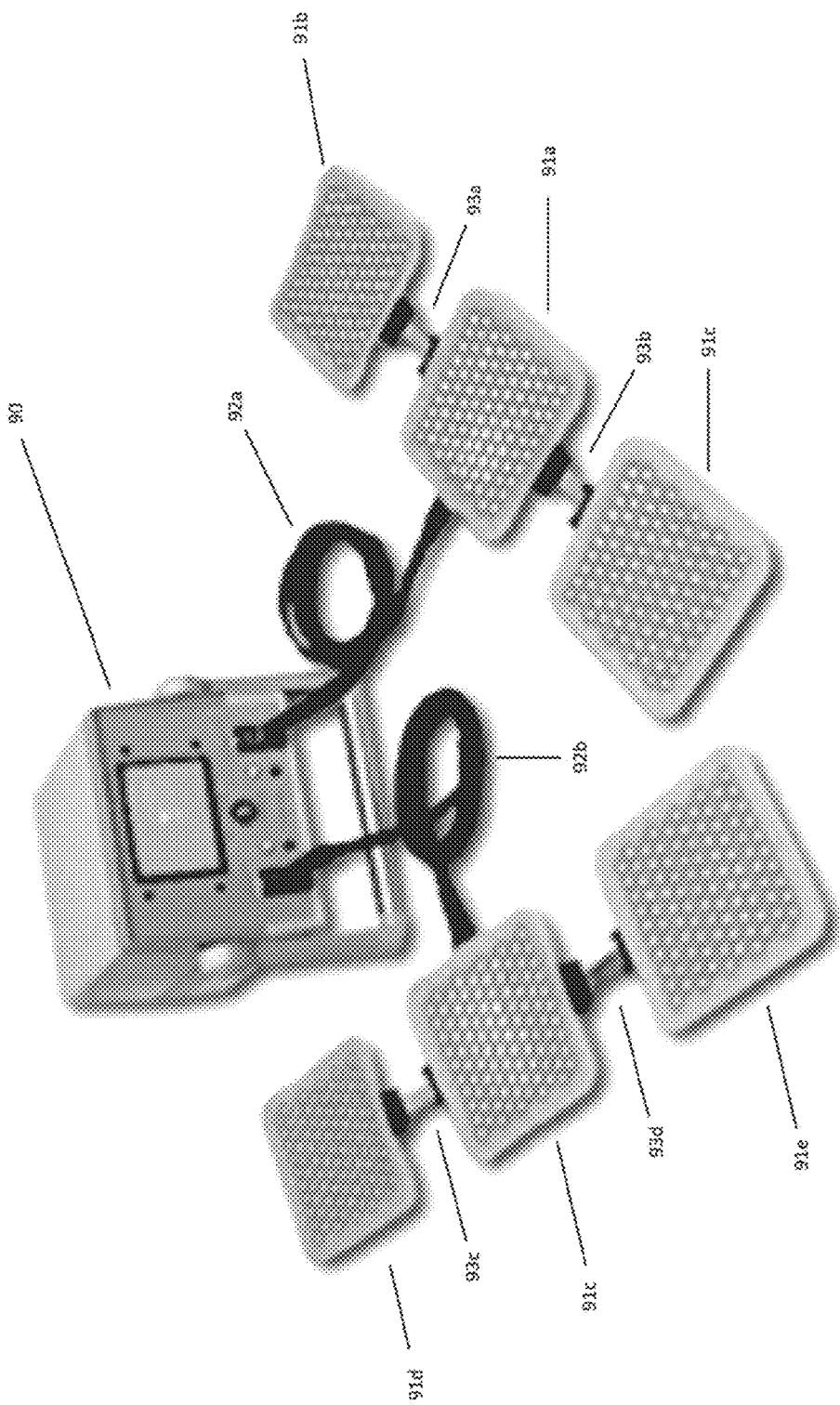
FIG. 5 is a pictograph of a prior art phototherapy system comprising dual sets of flexible LED pads.
Figure 6:
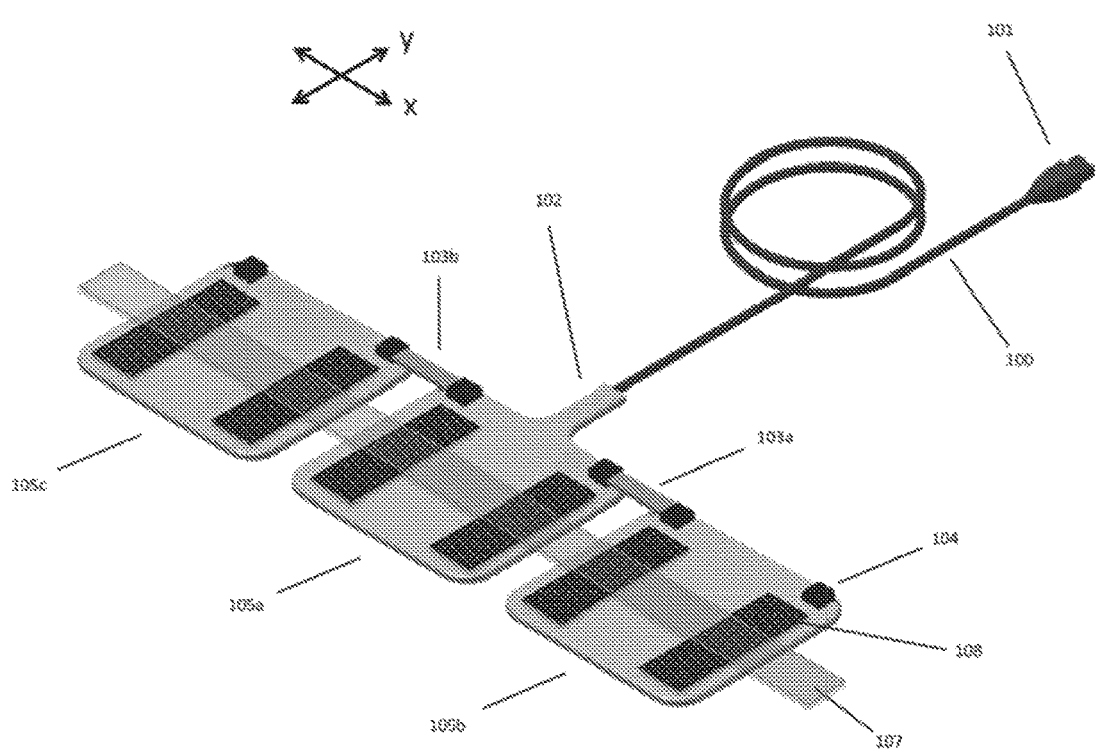
FIG. 6 is a plan view of a prior art flexible LED pad comprising a center and two side pads.
Figure 7:
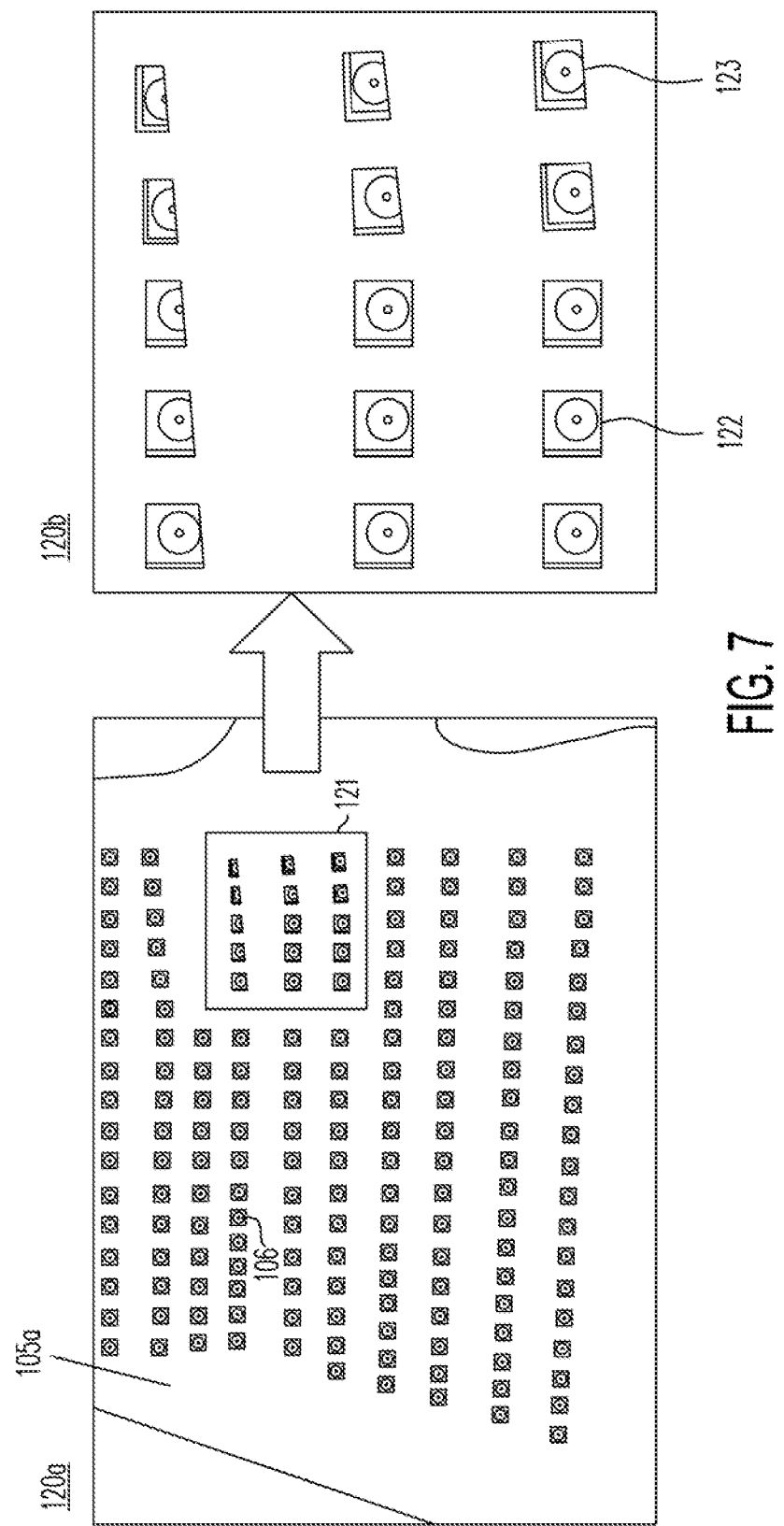
FIG. 7 is a pictograph of a prior art flexible LED pad depicting improperly positioned LEDs resulting, from repeated bending.
Figure 8:
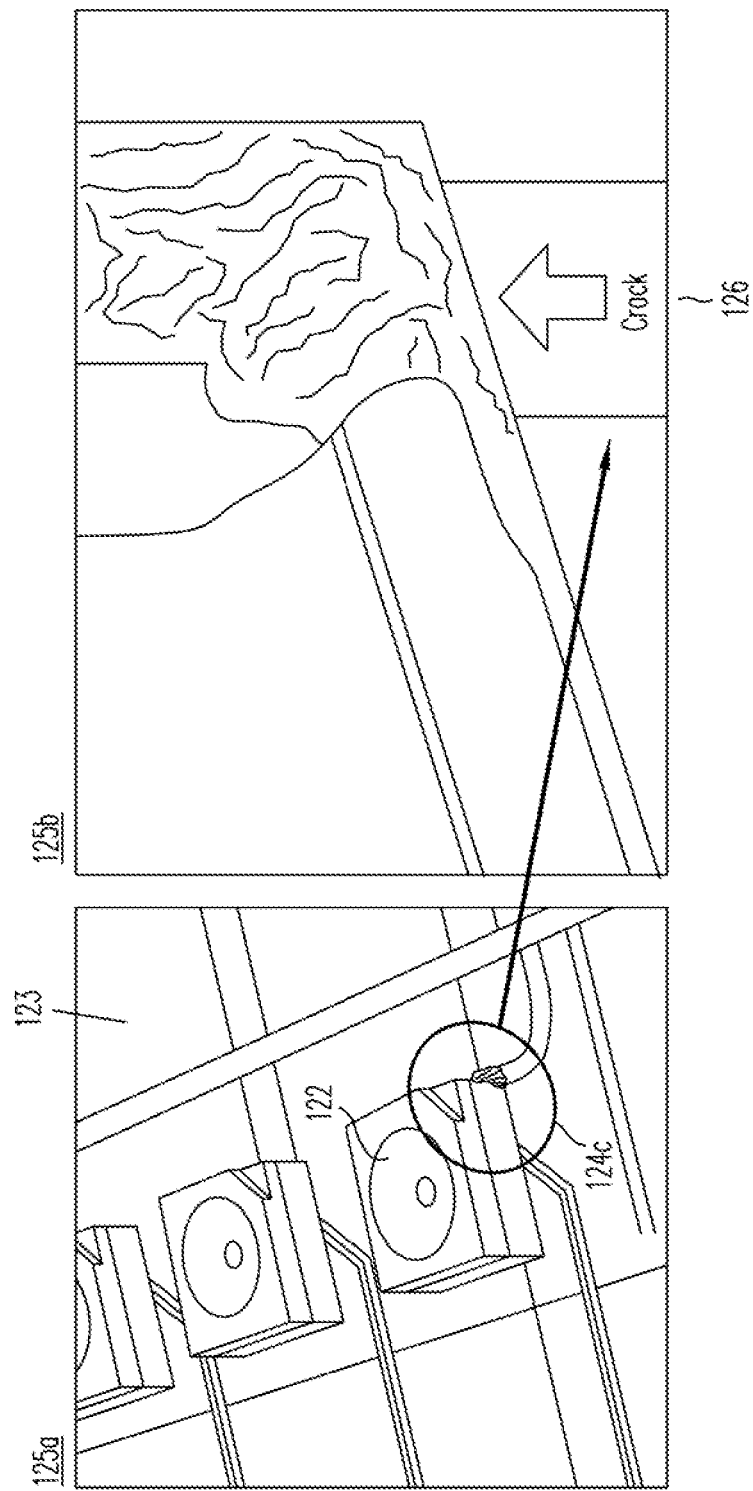
FIG. 8 is a pictograph of a prior art flexible LED pad depicting solder cracking between the LED lead and the flexible PCB conductor resulting from repeated bending.
Figure 9:
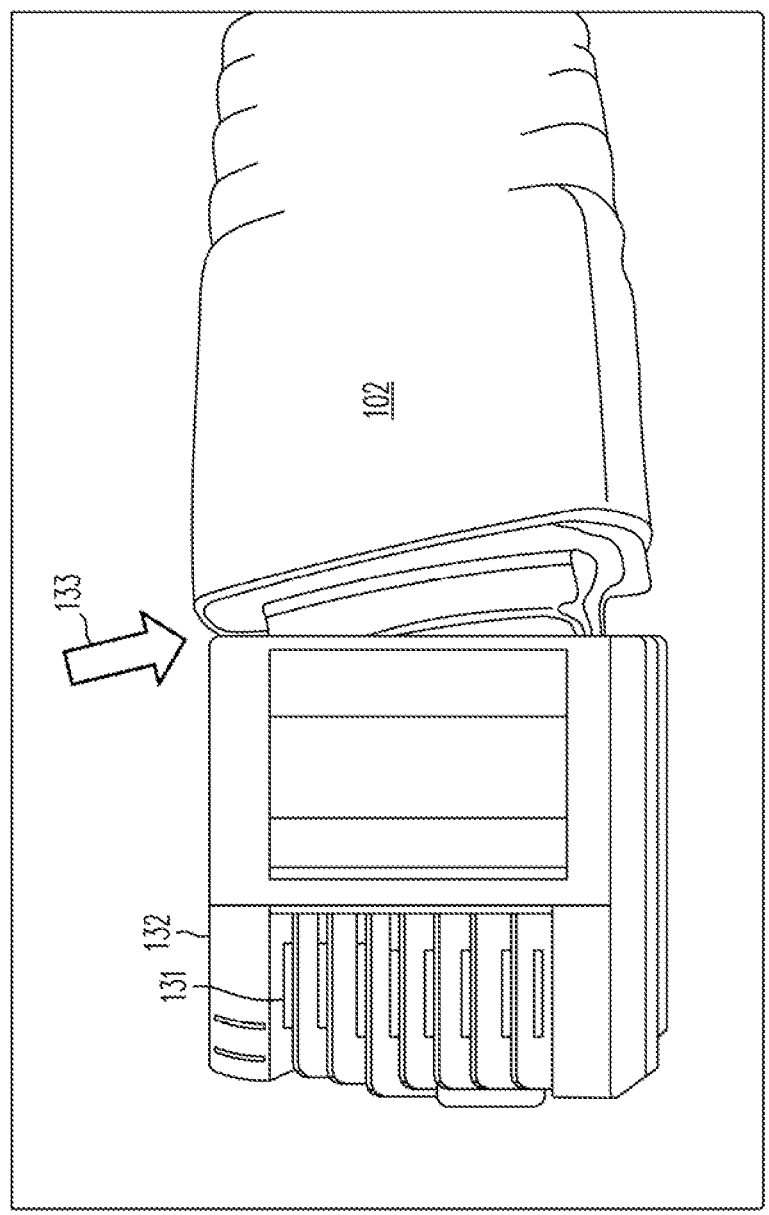
FIG. 9 is a pictograph of a prior art center LED pad cable depicting connector damage between the cable wire and the connector resulting from repeated use.
Figure 10:
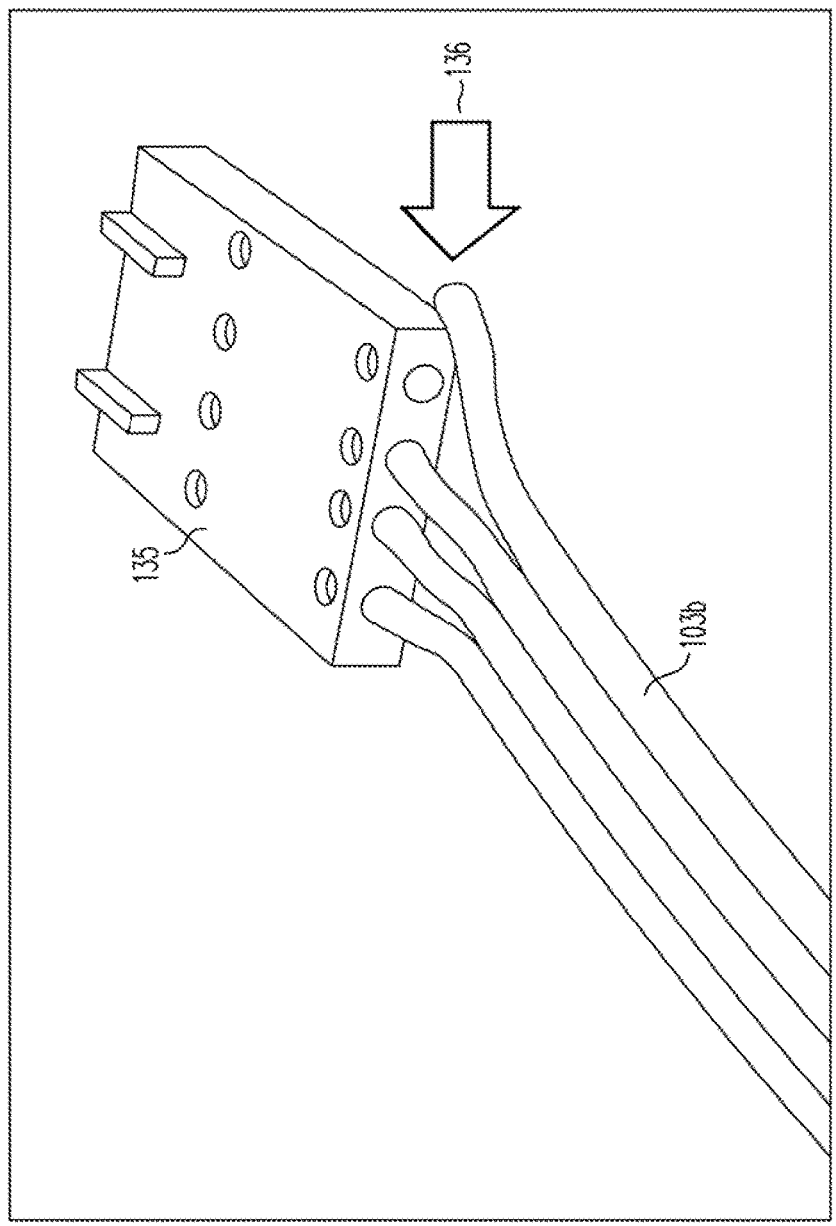
FIG. 10 is a pictograph of a prior art LED pad-to-pad cable depicting connector damage between the cable wire and the connector resulting from repeated use.
Figure 11:
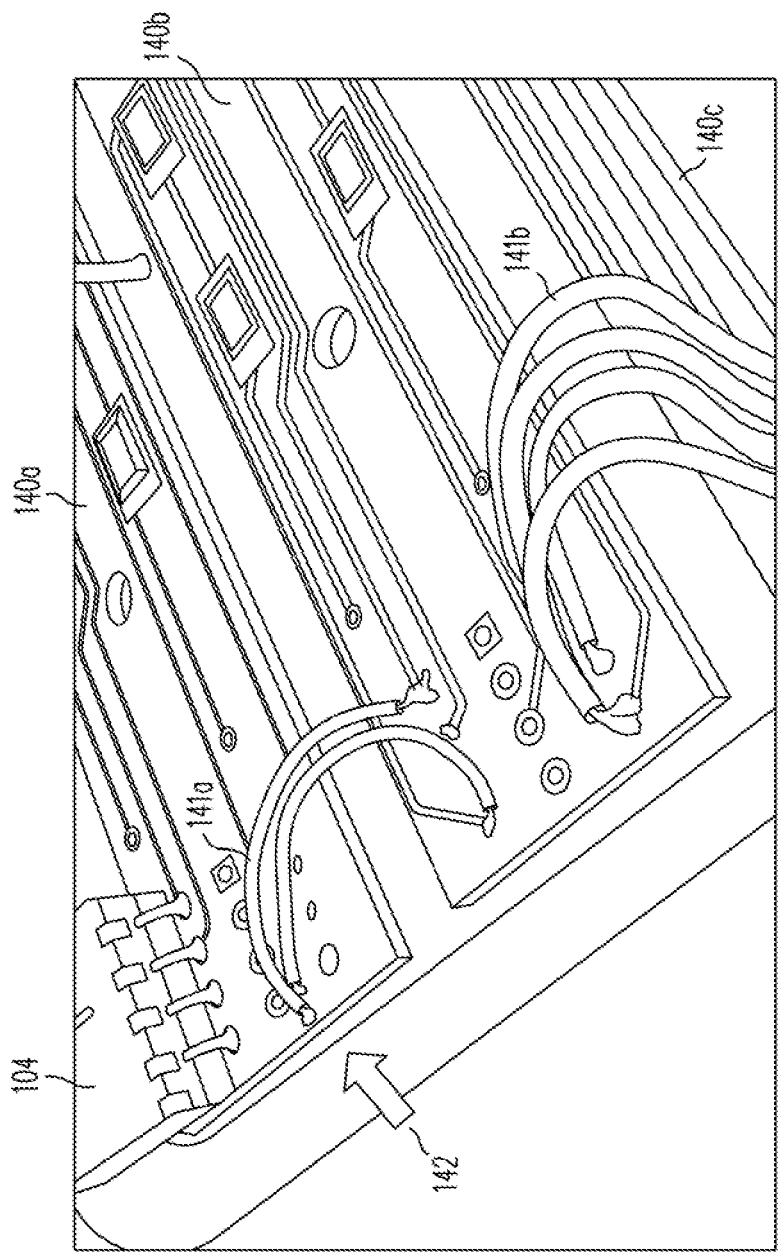
FIG. 11 is a pictograph of a prior art LED pad prototype illustrating broken wires connecting separate PCBs within a single LED pad.
Figure 12A:
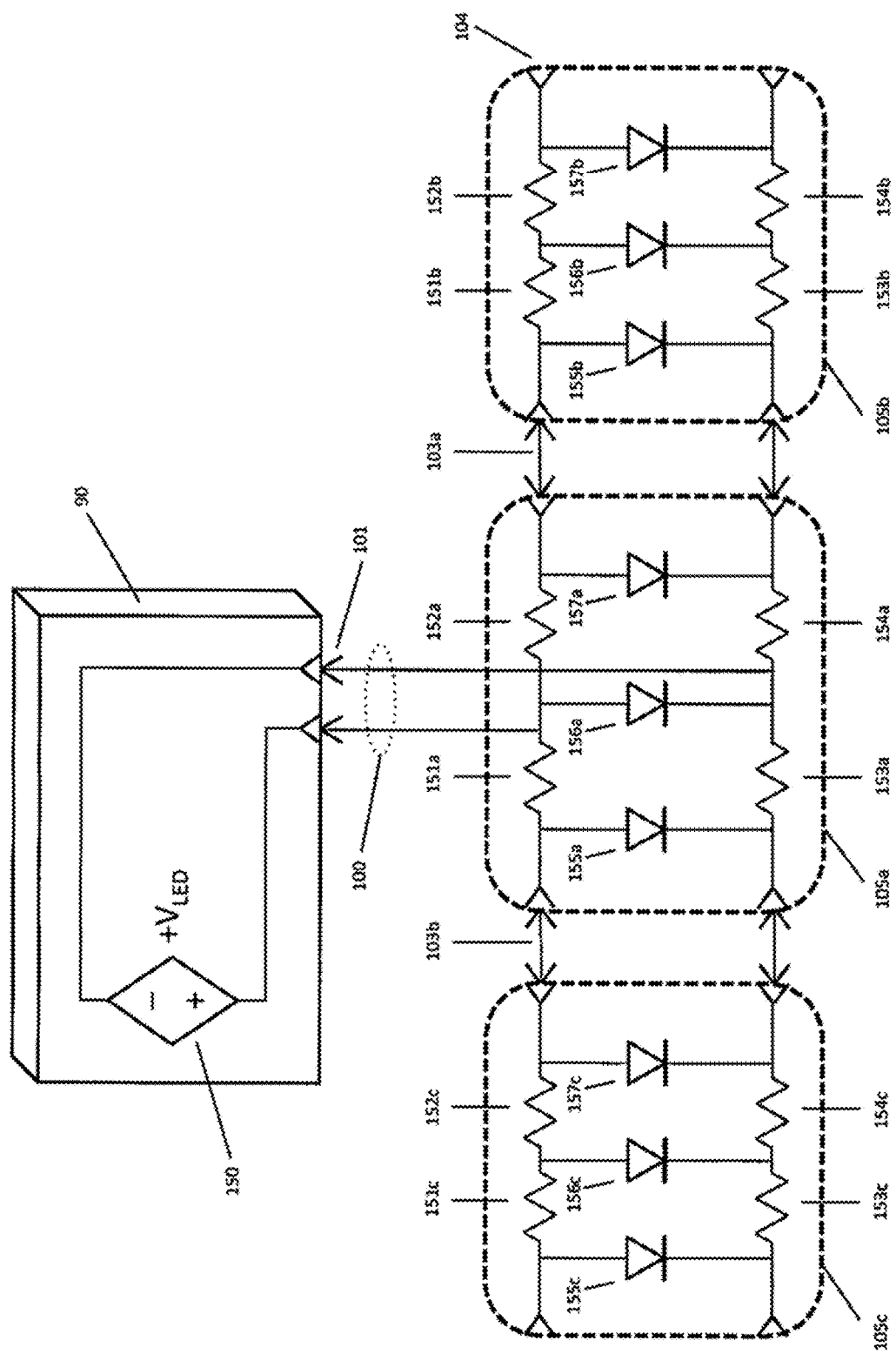
FIG. 12A is an electrical schematic representation of three LED pads connected to a LED controller in a T configuration.
Figure 12B:
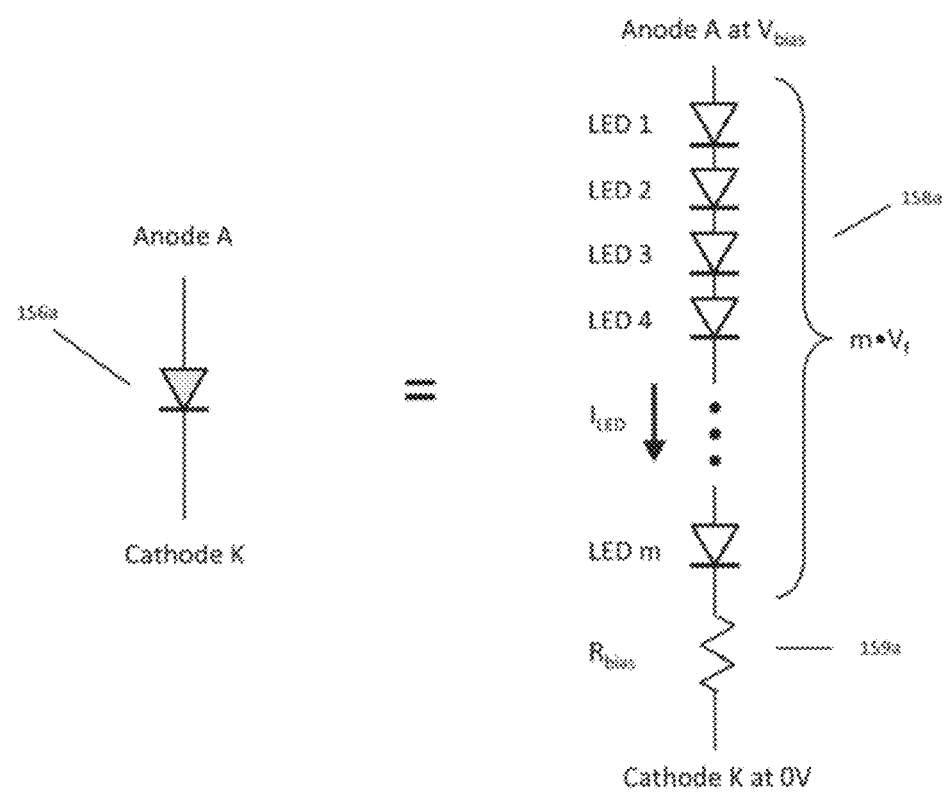
FIG. 12B is an electrical schematic representation of a single LED string comprising series connected LEDs and a bias resistor.
Figure 12C:
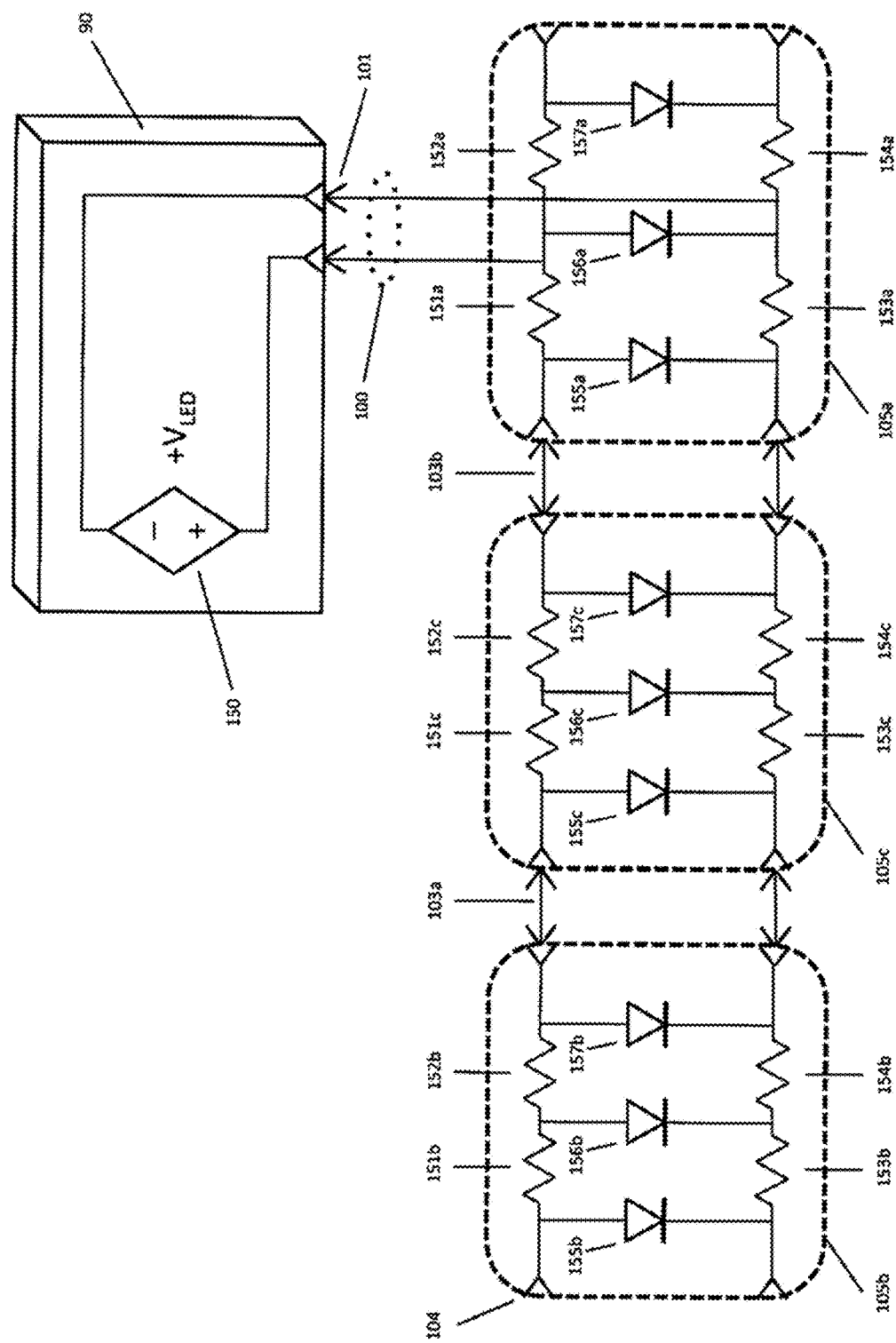
FIG. 12C is an electrical schematic representation of three LED pads connected to a LED controller in an L configuration.
Figure 13:
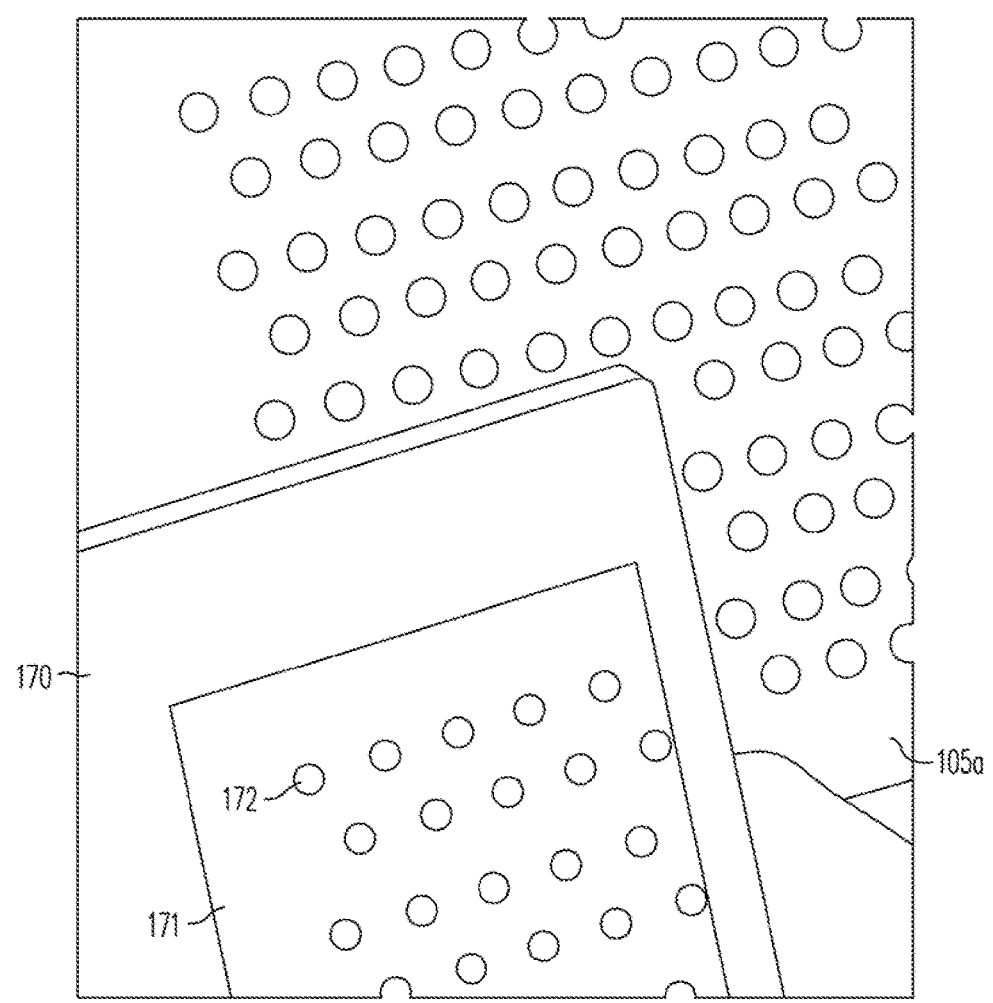
FIG. 13 is a pictograph of a prior art LED pad illustrating noise coupling resulting in simultaneous illumination of both red and infrared LEDs.

In the embodiment shown in FIG. 14A, center flexible LED pad 200a includes cable 202 and two USB sockets 204 all located on the same edge of rectangular shaped center LED pad 200a, as shown on the pad edge parallel to the x-axis. Similarly, in side LED pads 200b and 200c, each LED pad includes two USB sockets also located on the same edge of the rectangular shaped side LED pads. This connection scheme is markedly different from the prior art devices shown in FIG. 5 and FIG. 6 where the connector sockets are proprietary and located of opposite edge sides of the LED pads.

The benefit of this seemingly subtle design change of relocating the connectors is substantial, if not profound, greatly improving a physician's or clinician's choices in positioning the LED pads on a patient being treated. Because the connector sockets do not face one another as they do in prior art devices, the length of the connector cables 205a and 205b are not required to be made short in order to allow close placement of the LED pads. In fact, in the example shown, LED pads 200a, 200b and 200c may, if desired, actually abut, touching one another without putting any stress on the cables whatsoever, even if long cables are employed. With the LED pads touching, the versatility of the disclosed flexible LED pad set offers a doctor the ability to utilize the highest number of LEDs in the smallest treatment area.

Alternatively the flexible LED pads may be placed far apart, for example across the shoulder and down the arm, or grouped with two pads positioned closely and the third part positioned farther away, e.g. two pads used to cover the liver and kidney on the right side of the body and a third, pad positioned atop the left side kidney connected by a longer cable to the other two. With electrical shielding in cables 205a and 205b, the pads may be positioned fir apart without suffering noise sensitivity plaguing the prior art solutions shown previously.

Figure 4A:
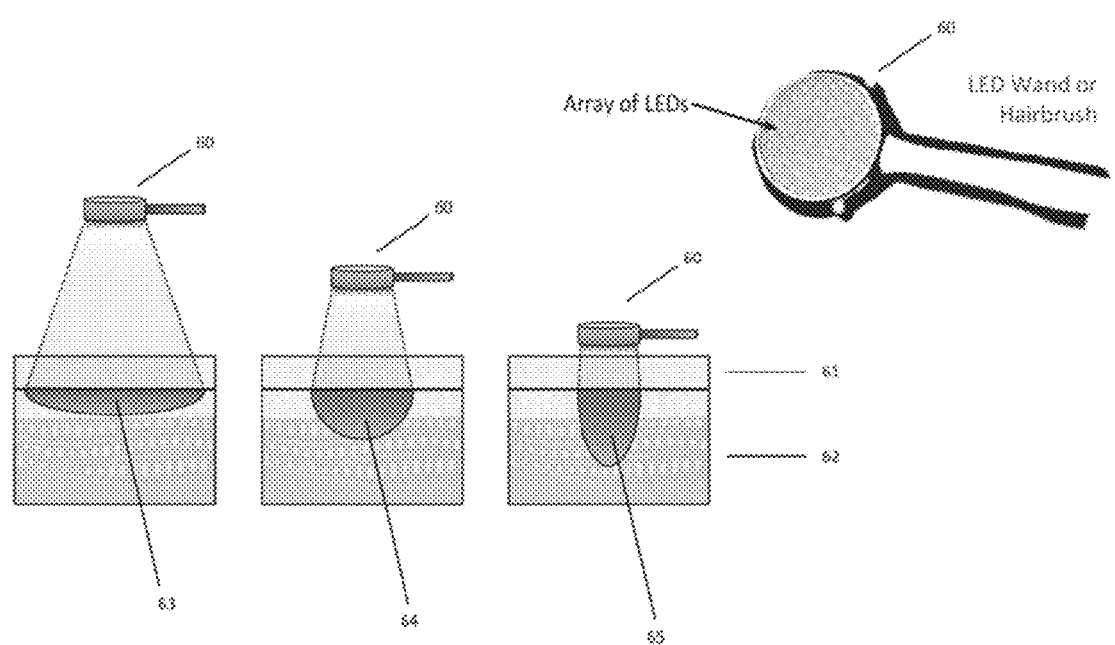
FIG. 4A is a schematic representation of phototherapy using a prior art handheld LED wand.
Figure 4B:
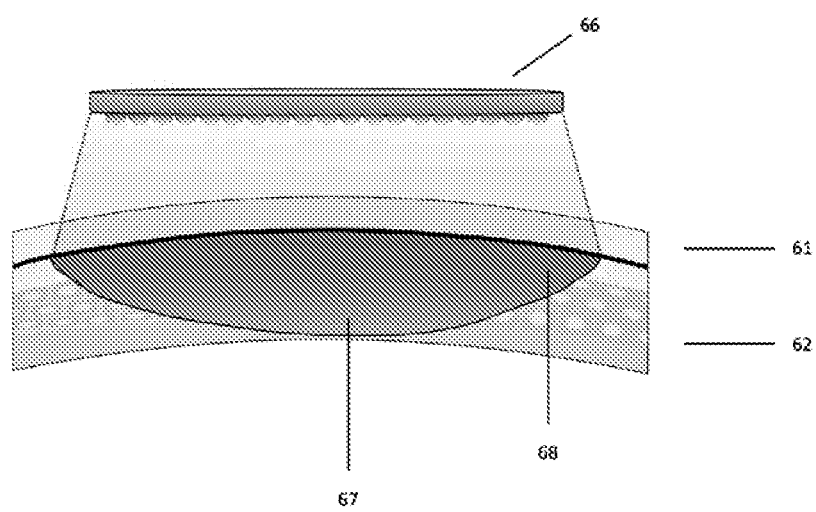
FIG. 4B is a schematic representation of phototherapy using a prior art stiff LED panel.
Figure 4C:
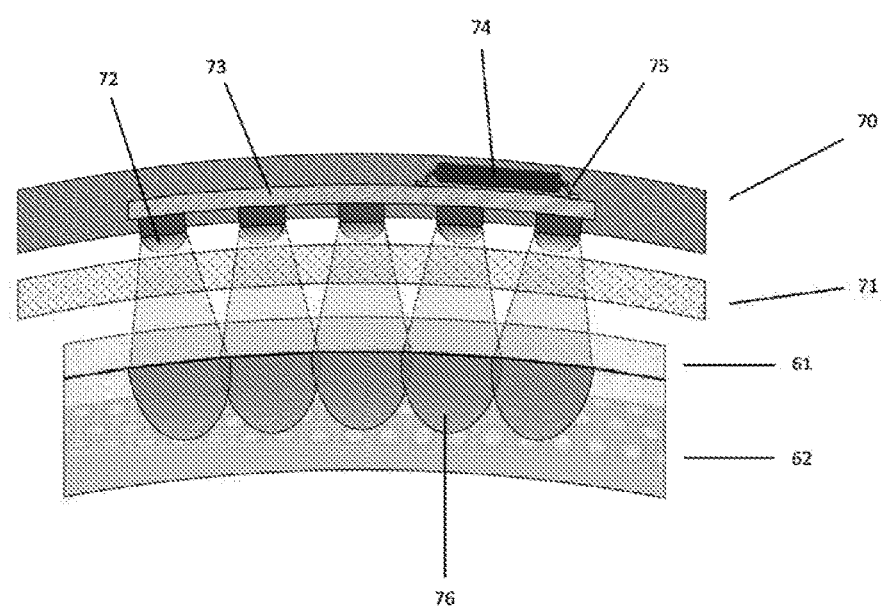
FIG. 4C is a schematic representation of phototherapy using a prior art flexible LED pad for treatment of a human patient.

The design shown in FIG. 14A also makes it easy for a clinician to position the flexible LED pads, bend them to fit to the patient's body, e.g. around the stomach and kidneys, and then secure the pads by Velcro belt 213 attaching to Velcro straps 212 attached firmly to the LED pads. The bending of the individual flexible LED pads and the Velcro belt binding them is illustrated in FIG. 4B, where the belt and the pads are bent to fit around a curved surface with curvature in the direction of the x-axis. In order to bend in the direction of the x-axis, no rigid PCB oriented parallel to the x-axis is embedded within the LED pad in this embodiment.

In this embodiment of the invention, one feature, the RJ45 connector 203 used to electrically connect the LED pad set to the LED controller has been preserved to maintain backward compatibility with the existing LED controllers already sold and operating in clinics and hospitals today. While the combination of RJ45 connector 203, cable 202, and cable-to-pad strain relief 201 may visually appear similar to the prior art pad set, the internal design is significantly different as will be described in later section of this disclosure in greater detail.

Lastly, it should be noted that the polymeric material comprising flexible LED pads 200 may be shaped according to the mold to include an embossed logo or identification mark 211, e.g. as company, hospital, clinic, or other logo, formed into and of the polymeric material itself. This embossing feature is very important for labeling purposes because the polymers acceptable to manufacture the LED pads must be chemically inert and biologically aseptic, and are therefore virtually impossible to print permanently on their surface with ink or dye. Using high-quality medical grade polymers like Teflon and medical-grade rubber-like materials, any ink printing will wash off and paper labels will peel off. Even securing Velcro straps onto the polymeric pads is a complex matter as will be discussed in the context of the polymer chemistry in a later part of this disclosure. As such, many of the drawings in the disclosure for the purposes of clarity do not illustrate any embossed logo or Velcro straps.

Figure 15:
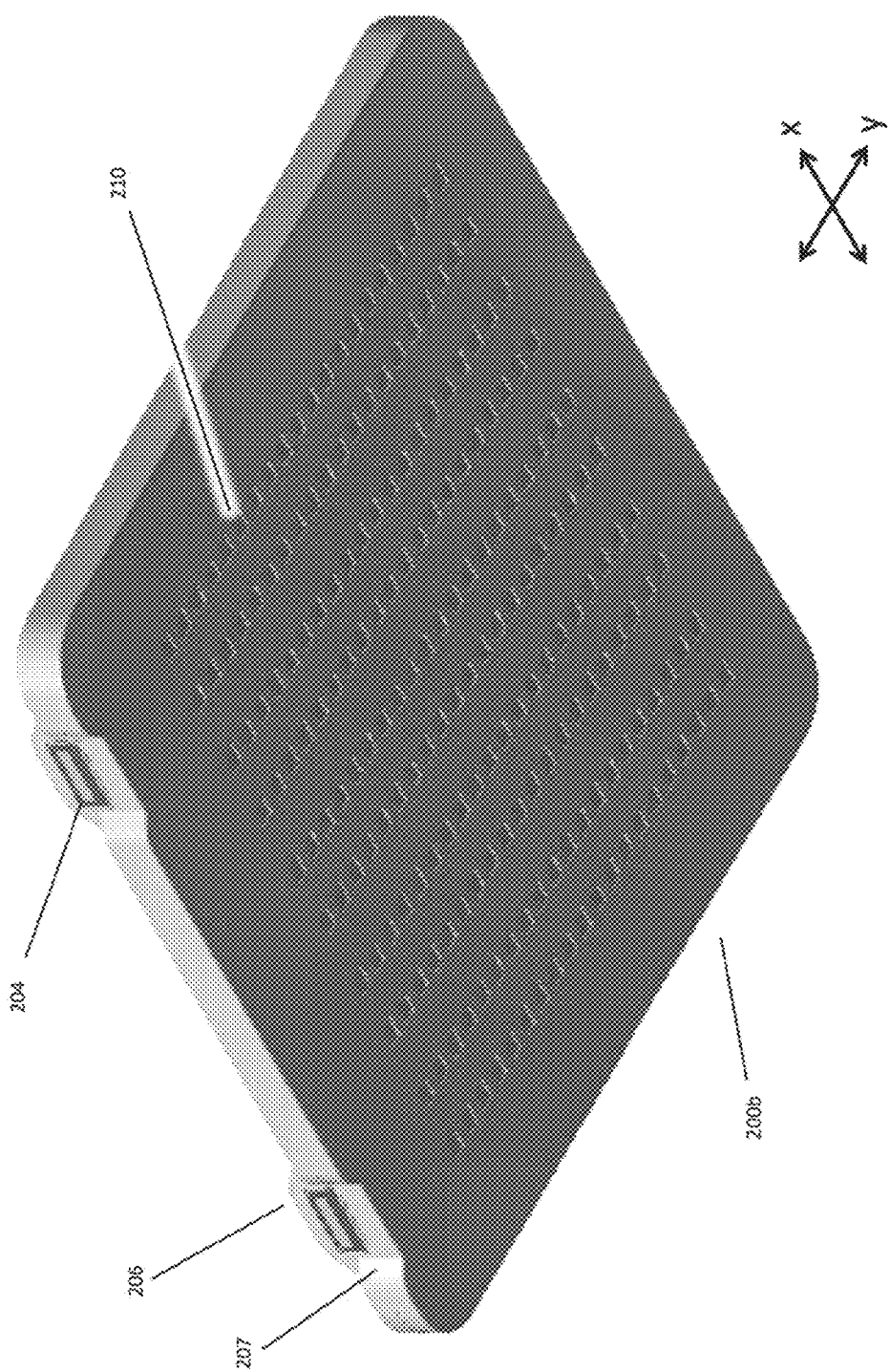
FIG. 15 is an underside perspective view of the side pad of the disclosed flexible LED pads.
Figure 16:
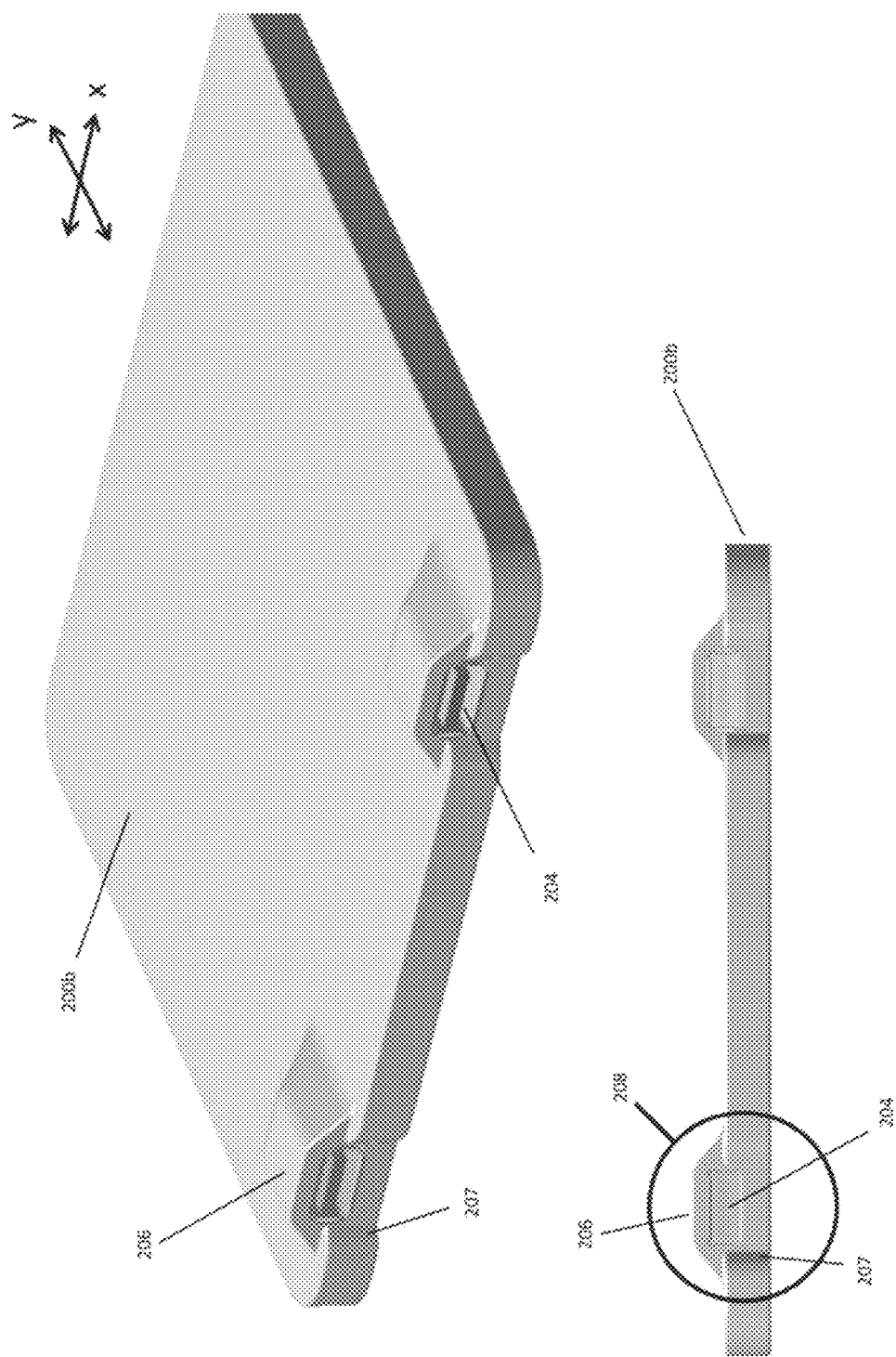
FIG. 16 is a top perspective and edge view of the side pad of the disclosed flexible LED pads.

FIG. 15 illustrates an underside perspective view and FIG. 16 illustrates a topside perspective view and edge view of one of the side flexible LED pads 200b (i.e. a side pad is defined herein as the LED pad without the hardwired cable 200 attached). Features of side LED pad 200b include openings 210 for the LED light to escape, USB connector sockets 204 located on one edge of the flexible LED pa, polymeric "bumps" 206 covering the top of USB connector sockets 204, and inset 207 to accommodate a corresponding USB plug. The USB connector region 208 is carefully designed to insure that the polymer forms around the USB connector, helping to "lock" it into place without peeling or delaminating during subsequent use. The shapes and cutout features used to secure the polymer to the USB socket 204 are molded into the polymeric pad during the injection or transport polymeric molding process and are not cut or trimmed ex post facto. Alternatively, the polymeric pad may be fabricated using a polymeric 3D printing process, but at a cost and throughput that may be unacceptable for mass production purposes.

Figure 17:
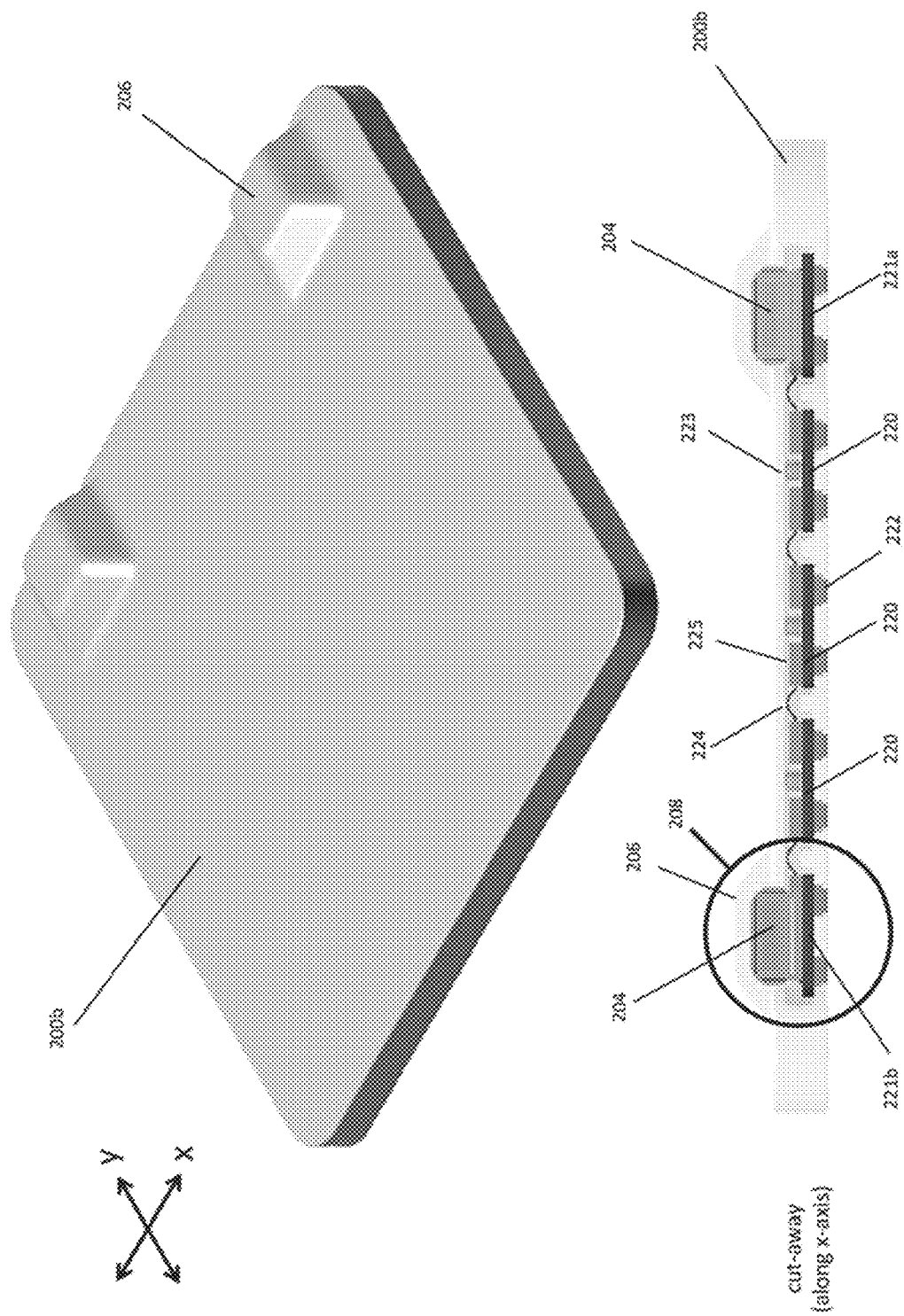
FIG. 17 is a top perspective and interior edge view of the side pad of the disclosed flexible LED pads.

FIG. 17 illustrates the edge cutaway view and corresponding top perspective view of flexible LED pad 200b. The edge view reveals the presence of five separate PCBs comprising left and right edge PCBs 211a and 211b to which are mounted USB sockets 204, and three identical symmetric PCBs 220 in between. The attachment of USB sockets 204 to the left and right edge PCBs 221b and 221a, respectively, naturally results in the characteristic feature of highlighted region 208 including polymeric bump 206. Atop the PCBs, various electronic components 223 such as capacitors, resistors, transistors or ICs, may be mounted along with low-profile electrical connectors, in this embodiment sockets 225. The individual PCBs are electrically connected by ribbon cables 224 with cable connectors on each end, in this embodiment plugs that are compatible with the low-profile sockets 225. Because the ribbon cables 224 are connected electrically to the PCBs 220, 221a and 221b through a plug and socket arrangement, no wires or cables are soldered directly onto the PCB. LEDs 222 are mounted to the undersides of PCBs 220, 221a and 221b. In other embodiments, low-profile sockets could be used instead of plugs for the cable connectors, and low-profile plugs instead of low-profile sockets 225 could be used for the electrical connectors mounted to the PCBs.

Figure 18:
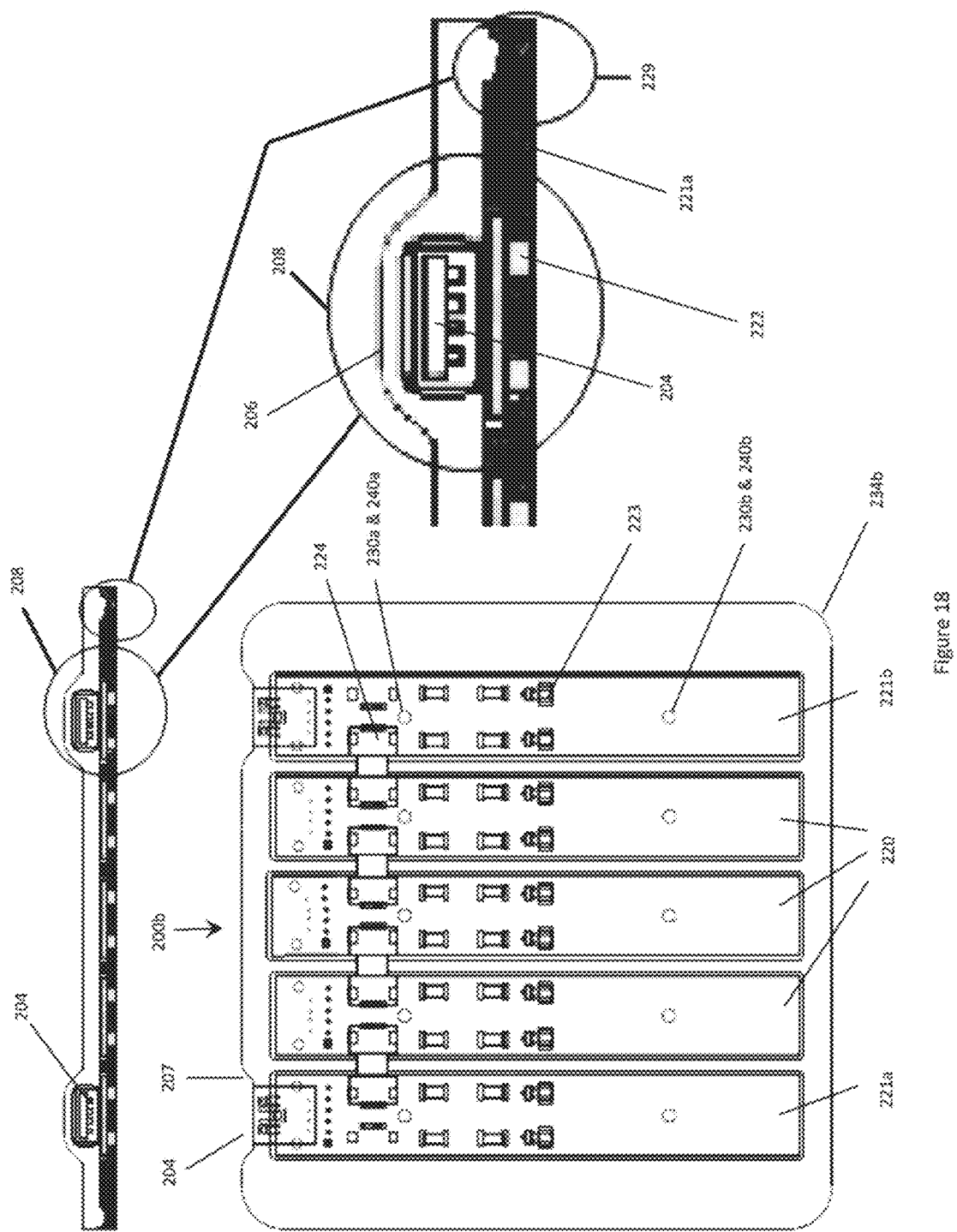
FIG. 18 is a top and edge view from the CAD schematic file of the side pad and internal PCB of the disclosed flexible LED pads.

Details of the PCBs are further elaborated on the CAD drawing shown in FIG. 18 as a top view and edge view of flexible LED pad 200b including a left edge PCB 221a, a right edge PCB 221b, and three intervening symmetric PCBs 220. Region 208 is further expanded to illustrate the polymeric "bump" 206 covering connector 204 on the left and right edge PCBs 221a and 221b, including LEDs 222 located below blow the PCBs. Every PCB shown includes a ribbon cable connector 224 and surface mount components 223.

Figure 19A:
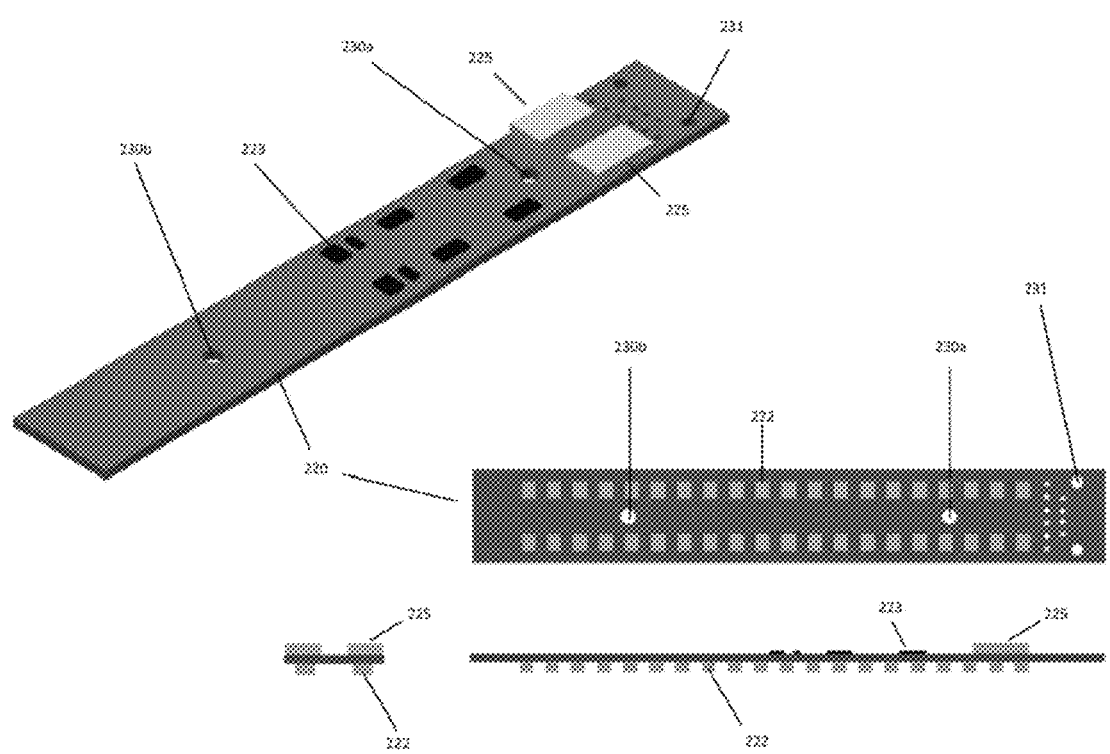
FIG. 19A shows top perspective, underside, widthwise and lengthwise edge views of the internal PCB contained within the disclosed flexible LED pads.

The "symmetric" PCB 220 is shown in greater detail in FIG. 19A, in a top perspective view, in a bottom side view, and by edgewise and lengthwise view. As shown, the holes for polymeric posts 230a and 230b are included along with surface mount components 223 and ribbon-cable connector sockets 225 used to facilitate PCB-to-PCB connections. The underside of PCB 220 reveals the positioning of an array of LEDs 222 soldered onto the PCB and comprising two columns of twenty LEDs each. Each LED comprises a single light-emitting-diode semiconductor chip housed in a plastic package with a transparent optical lens top, i.e. one LED chip per package. As a result, each PCB holds and controls 40 LEDs assuming a single LED per package. With five PCBs each holding 40 LEDs, flexible LED pad 200b contains 200 LEDs.

If the LEDs are arranged in series-connected strings of LEDs, two per PCB, then one LED pad comprises 10 strings. If each string conducts 30 mA max each, the total current per LED pad is 300 mA. PCB 220 is referred to as a symmetric PCB because the PCB includes two ribbon-cable sockets 225 facing the adjacent PCBs in the flexible LED pad assembly. The ribbon cable sockets 225 are soldered into the conductive traces on PCB 220. No wire is soldered into the PCB. While the PCB includes, mounting holes 231 that are designed for USB sockets, the symmetric PCBs do not include any such socket, so the holes are left open. The rigidity of the PCB prevents cracking of the solder where the leads of LEDs 222 and the leads of surface mount components 223 touch the conductive traces on PCB 220.

Figure 19B:
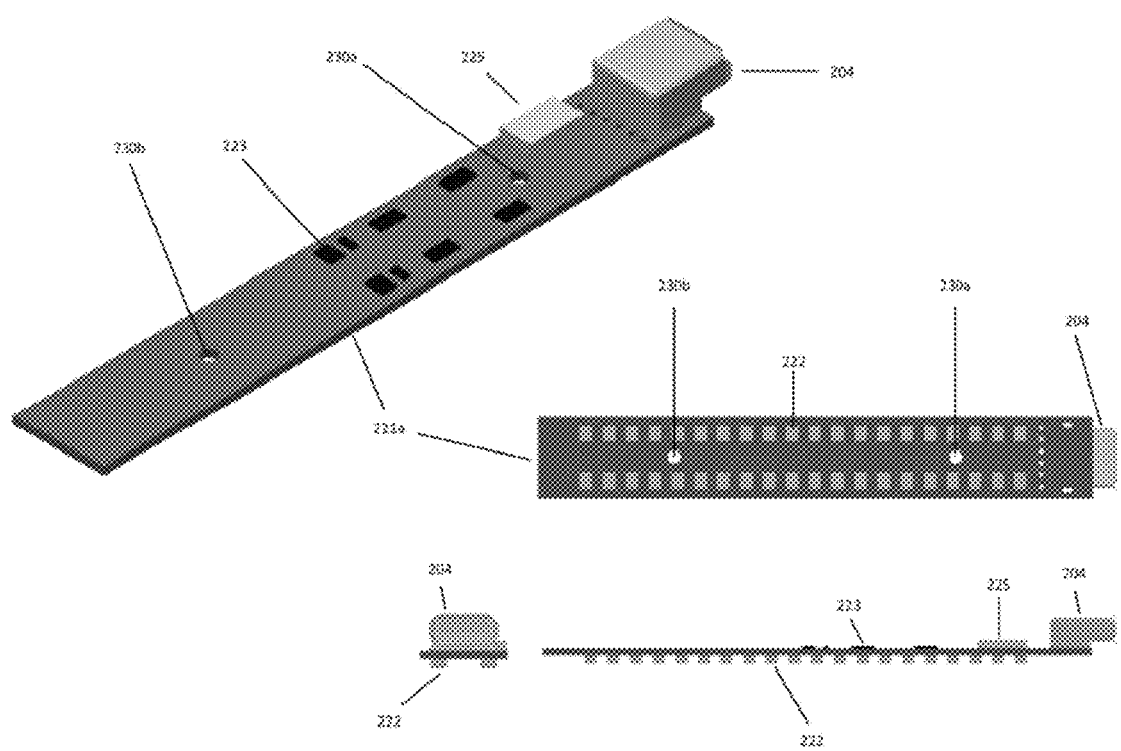
FIG. 19B shows top perspective, underside, widthwise and lengthwise edge views of an left-edge PCB contained within the disclosed flexible LED pads.

FIG. 19B illustrates the same four perspective, underside, and edge drawing as the prior figure except for left edge PCB 221a. This drawing shows USB socket 204 is mounted at the end of PCB 221a which also includes the same mounting holes for polymer posts 230a and 230b. PCB 221a is referred to as a left edge PCB because it is positioned along the left edge of flexible LED pad 200b (as shown in FIG. 18). As such, it includes USB socket 204 and has only a single ribbon cable socket 225.

Figure 19C:
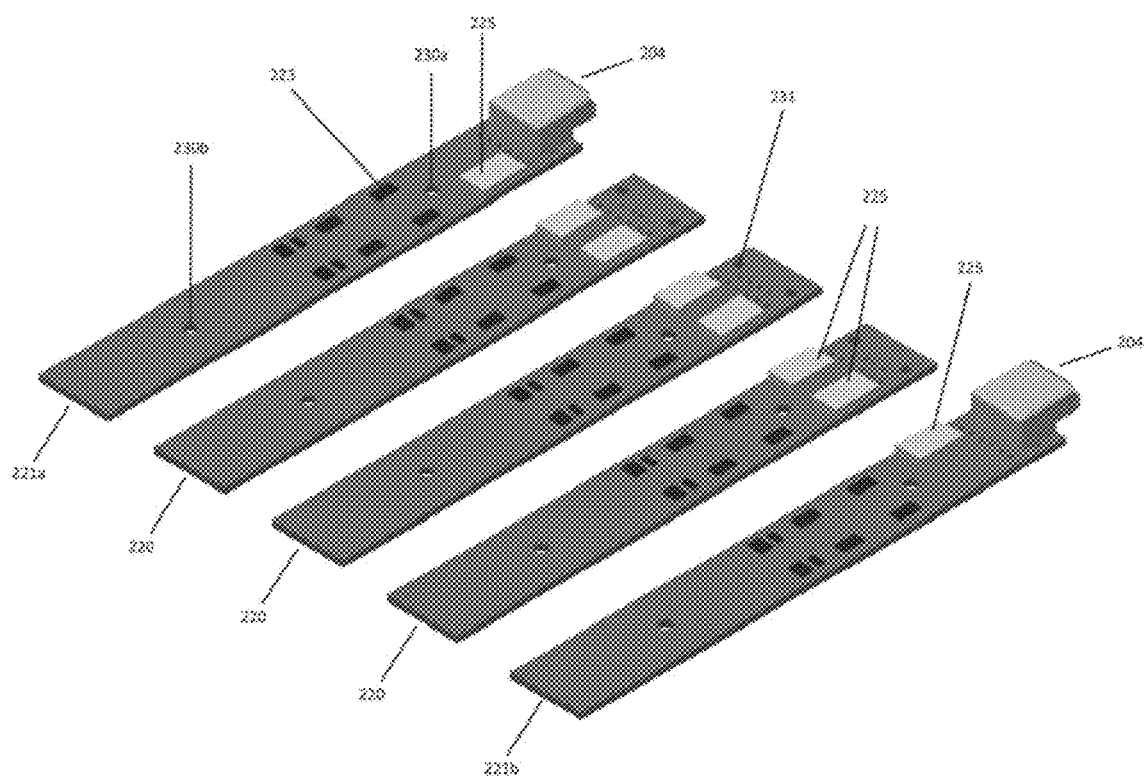
FIG. 19C is an exploded top perspective view of the set of PCBs contained within the disclosed flexible LED pads including left-edge, internal, and right-edge PCBs.
Figure 19D:
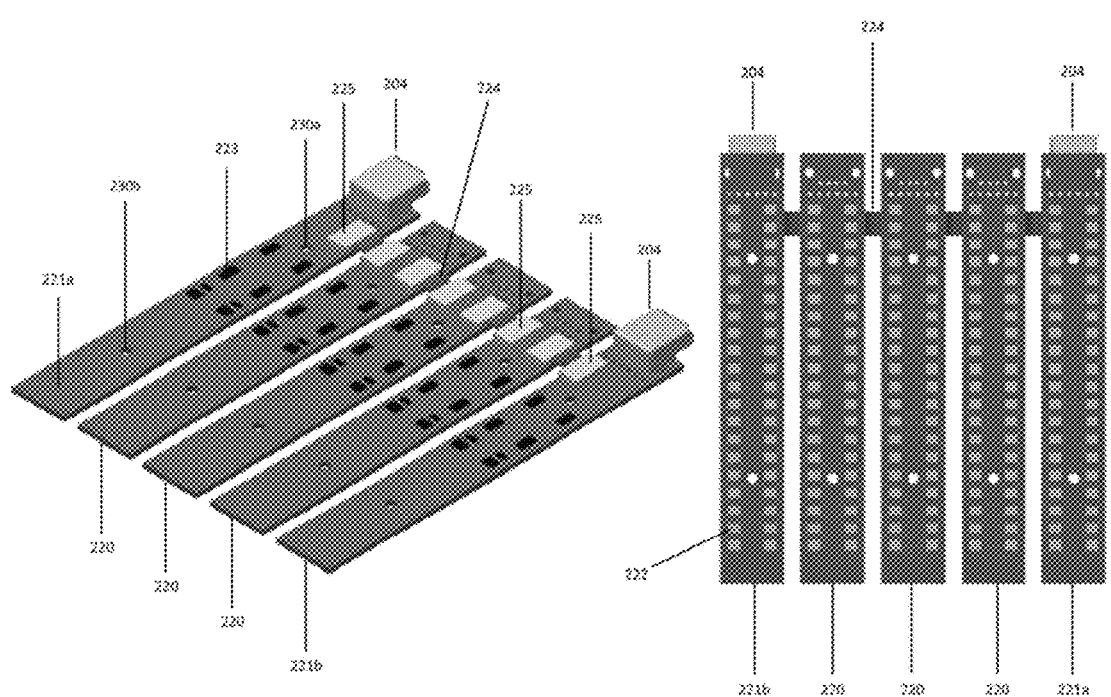
FIG. 19D is a top perspective and underside view of the PCBs contained within the disclosed flexible LED pads including ribbon-cable connectors.

FIG. 19C illustrates an exploded view of the five PCBs in their relative positions, including the right edge PCB 221b with its one ribbon cable socket 225 and its USB socket 204, the three intervening symmetric PCBs 220, each having no USB socket and two ribbon-cable sockets 225, and the left edge PCB 221a with its one ribbon cable socket 225 and its USB socket 204. FIG. 19D illustrates a top perspective view and underside view of the same five PCBs in their proper relative positions, including ribbon cables 224 interconnecting all the PCBs.

Figure 20A:
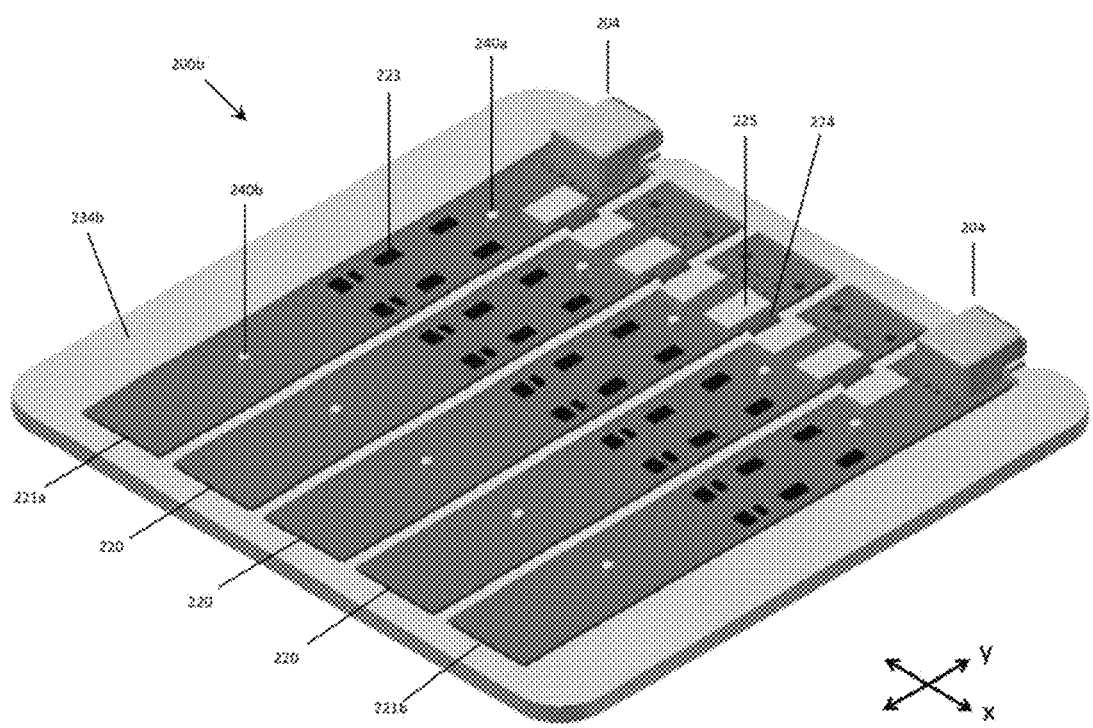
FIG. 20A is a top perspective interior view of the side pad of the disclosed flexible LED pads including the PCBs contained within.
Figure 20B:
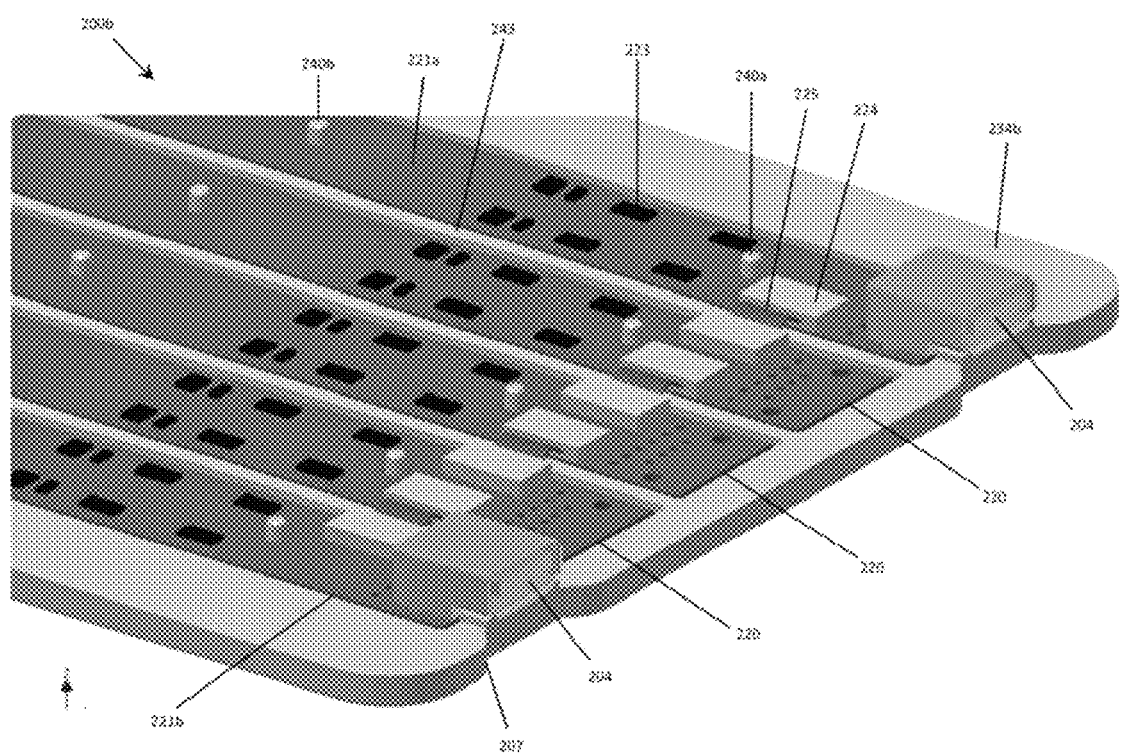
FIG. 20B is a top perspective interior end view of the side pad of the disclosed flexible LED pads including the PCBs and connector sockets contained within.

FIG. 20A illustrates the aforementioned assembly of PCBs 221a, 221b and 220 is positioned into downsets or recesses in a bottom polymeric piece 234b of flexible LED pad 200b where the polymeric posts 240a and 240b protrude through holes 230a and 230b in the PCBs 221a, 221b and 220, securing PCBs 221a, 221b and 220 from moving within the LED pad 200b and keeping the LED array which is attached to PCBs 221a, 221b and 220 aligned with the holes in the pad. FIG. 20B shows a close-up view of the bottom piece 234b of flexible LED pad 200b, illustrating that the PCBs 221b, 220 and 221a sit in a downset of the polymeric pad bottom piece 234b with a surrounding polymeric, ridge 243 around each of PCBs 221a, 220 and 221b. This downset and its corresponding ridge 243, along with the polymeric posts 240a and 240b, help hold the PCBs 221a, 220, and 221b and LEDs in place within the flexible LED pad 200b.

Figure 21B:
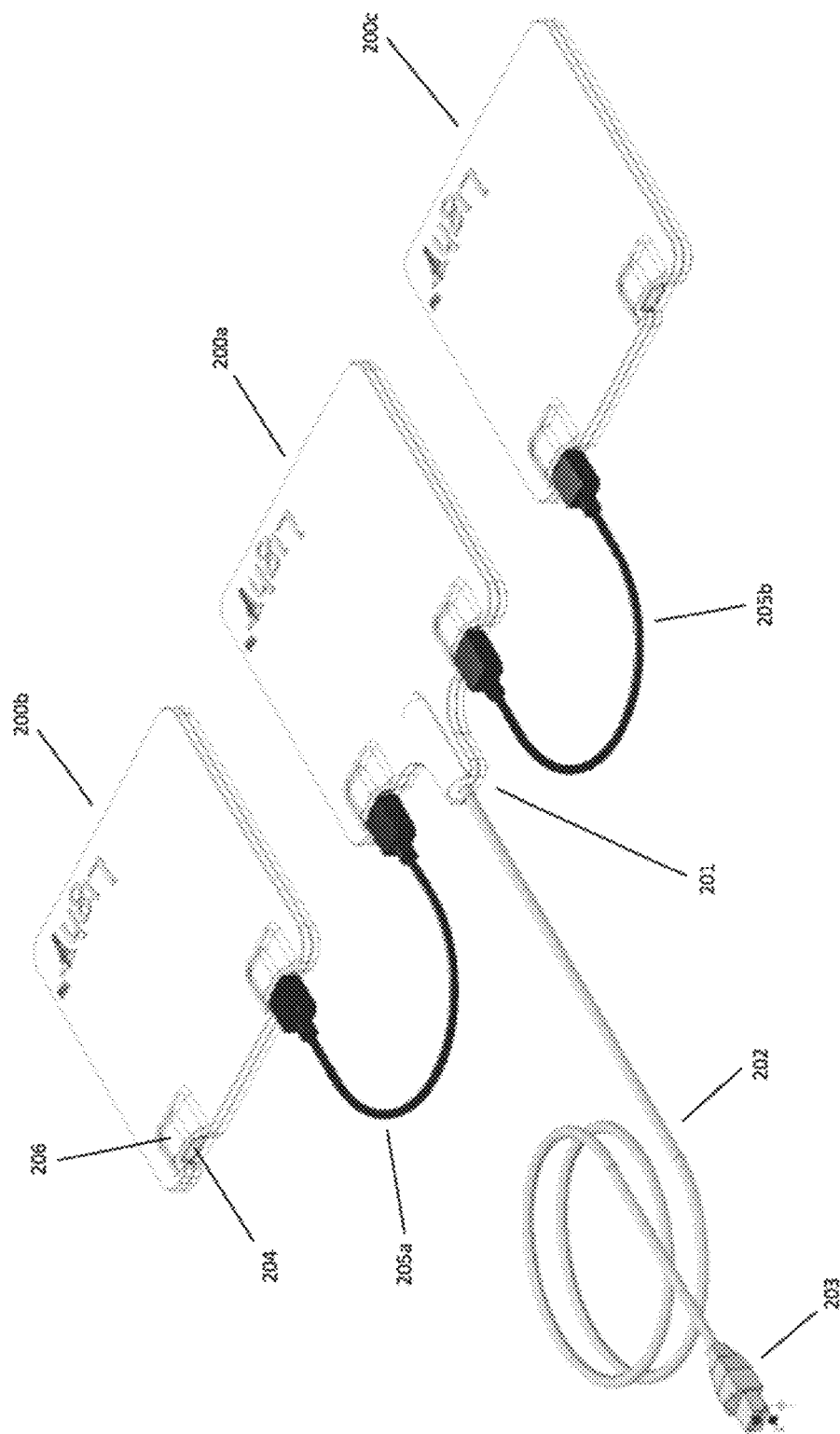
FIG. 21B is a view of the disclosed flexible LED pad comprising a center pad with integrated connecting cable, two side pads, and two pad-to-pad connectors connected in a T configuration.
Figure 21C:
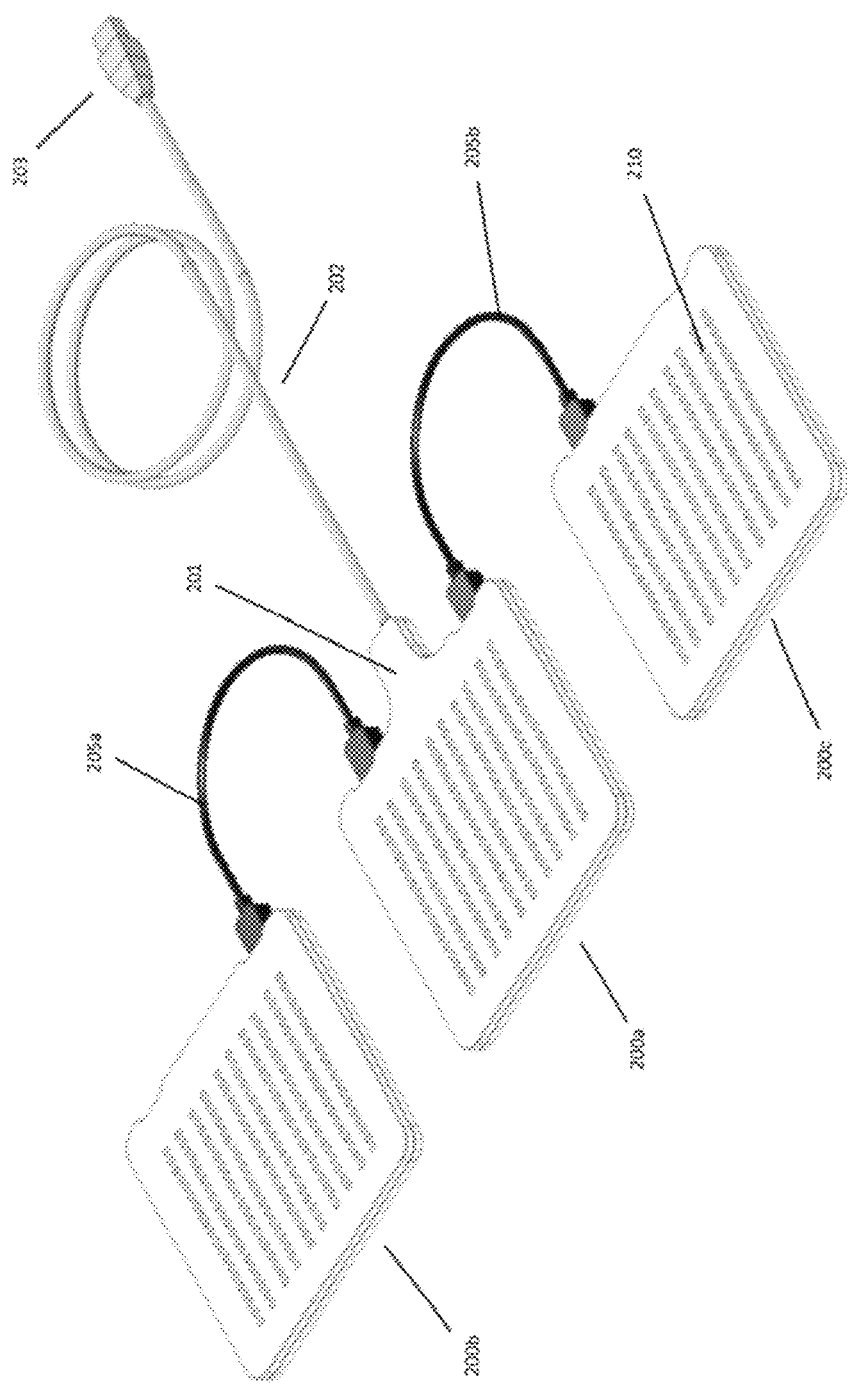
FIG. 21C is an underside view of the disclosed flexible LED pad comprising a center pad with integrated connecting cable, two side pads, and two pad-to-pad connectors connected in a T configuration.

Combining the aforementioned elements, FIG. 21A illustrates a perspective view of a set of three LED pads comprising center and two edge flexible LED pads 200a, 200b and 200c respectively, cable 202 with strain relief 201 and RJ45 plug 203, USB sockets 204, and USB cables 205a and 205b. FIG. 21B illustrates the same flexible pad set connected in a T configuration similar to FIG. 14A but absent the Velcro straps and Velcro belt. FIG. 21C shows the underside of the flexible LED pad set connected in a T configuration revealing the openings 210 in the flexible polymeric pads for LEDs.

FIG. 22 illustrates a close-up underside perspective drawing of center flexible LED pad 200a, illustrating cable 202 with strain relief 201 along with USB sockets 204 and revealing the pad openings 210 for LEDs. The purpose of strain relief 201 is to facilitate strain relief for cable 202 to prevent damage to internal solder joints.

Figure 23:
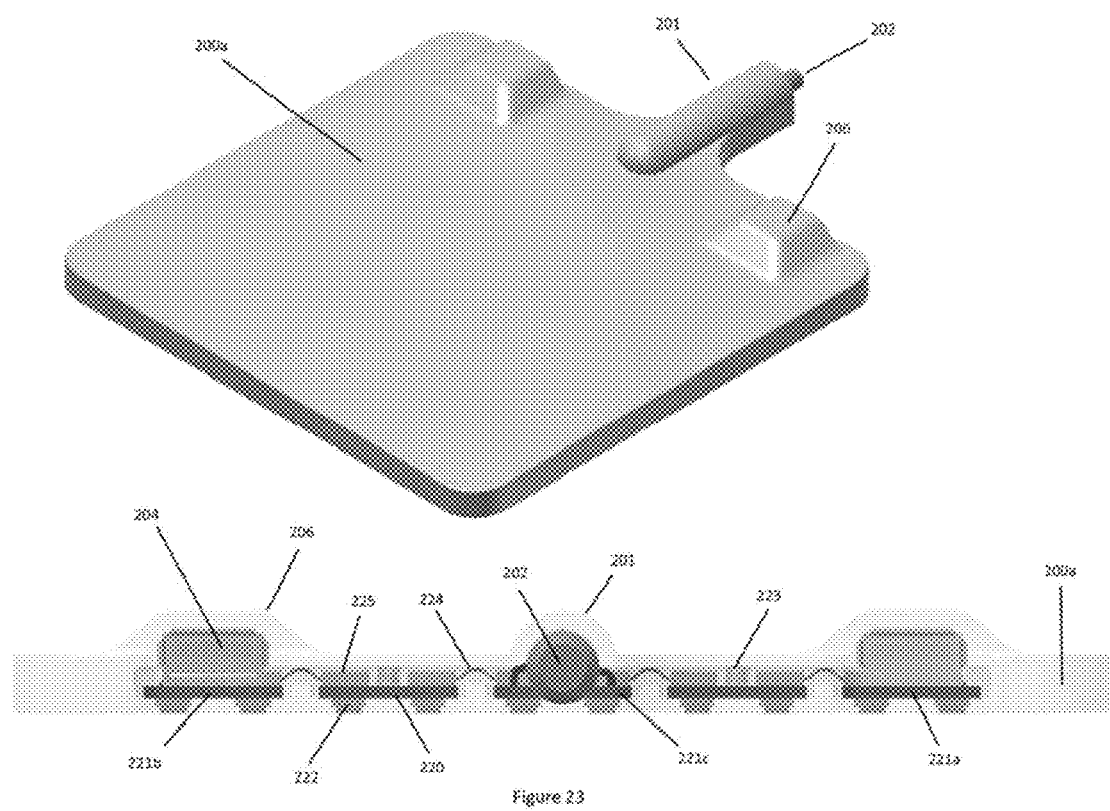
FIG. 23 is a top perspective and interior view of the center pad of the disclosed flexible LED pads including the PCBs contained within.

FIG. 23 illustrates the edge cutaway view and corresponding top perspective view of center flexible LED pad 200a. The edge view reveals the presence of five separate PCBs comprising, left and right edge PCBs 211a and 211b including USB sockets 204, center PCB 221c with cable 202 and strain relief 201 and two symmetric PCBs 220 in between. The inclusion of USB sockets 204 on the left and right edge PCBs naturally results in the characteristic polymeric bump 206. The underside of the PCBs includes LEDs 222 mounted on each PCB. Atop the PCBs, various electronic components 223 such as capacitors, resistors, transistors or ICs, may be mounted along with low-profile sockets 225. The individual PCBs are electrically connected by ribbon cables 224 with plugs on each end compatible with the low-profile sockets 225. Because the ribbon cables 224 are connected electrically to the PCBs through a plug and socket arrangement, no wires or cables for PCB-to-PCB interconnections are soldered directly onto the PCB, but cable 202 does involve soldered wires connected into PCB 221c.

Figure 24:
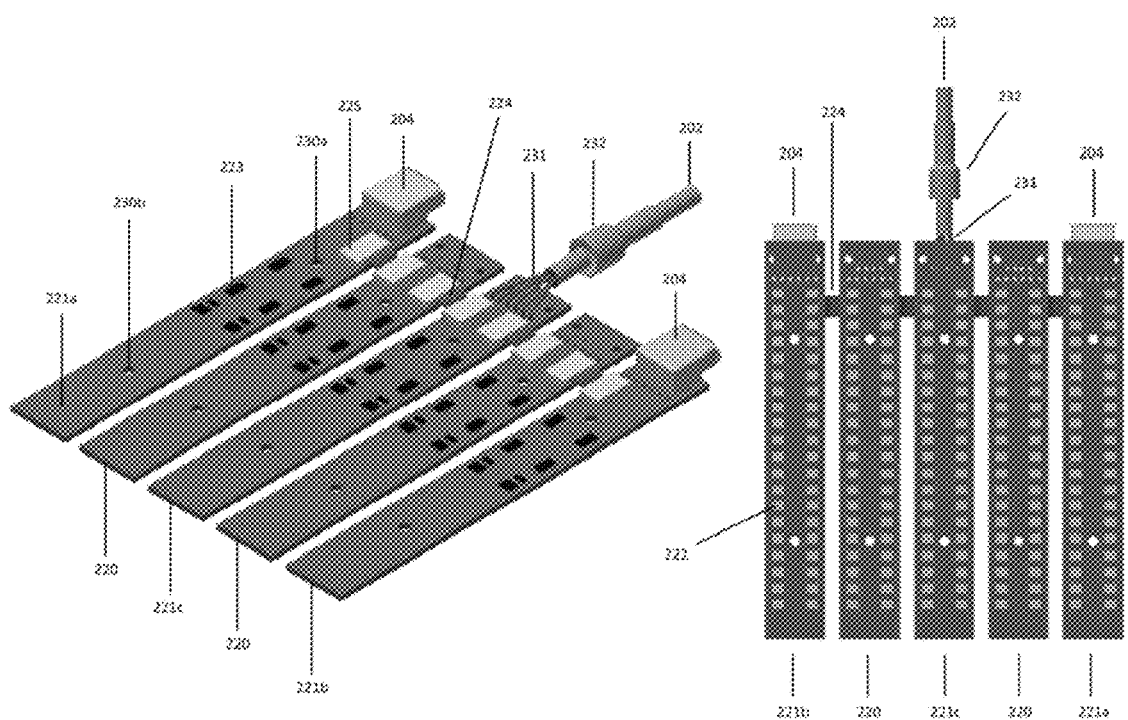
FIG. 24 is a top perspective and underside view of the PCBs contained within the disclosed flexible LED pads including ribbon-cable connectors and integrated connector cable.

FIG. 24 illustrates the top perspective view and underside view of the five aforementioned PCBs sequentially left to right from above as 221a, 220, 221c, 220, and 221b in their proper relative position including ribbon cables 224 interconnecting all the PCBs. The design is similar to the design of the PCBs used in the edge flexible LED pads 200b shown in FIGS. 15-18 and 19A-19D except that in the center pad 200a the middle symmetric PCB 220 is substituted by center PCB 221c, including soldered connections to cable 202 through individual wires 231. Otherwise, the construction of center PCB 221c is similar to that of symmetric PCBs 220 including surface mounted components 223, holes 230a and 230b for polymeric posts, and the underside array of LEDs 222. Because wires 231 are soldered to center PCB 221c, the risk of a "pulling force" on cable 220 has the potential to rip the wires from the PCB resulting in one or more cracked solder joints or broken wires and a resulting open circuit. As described below, a collar 232, crimped into position on cable 202 contacts a notch on the inside of strain relief 201 to prevent this from happening.

Figure 25A:
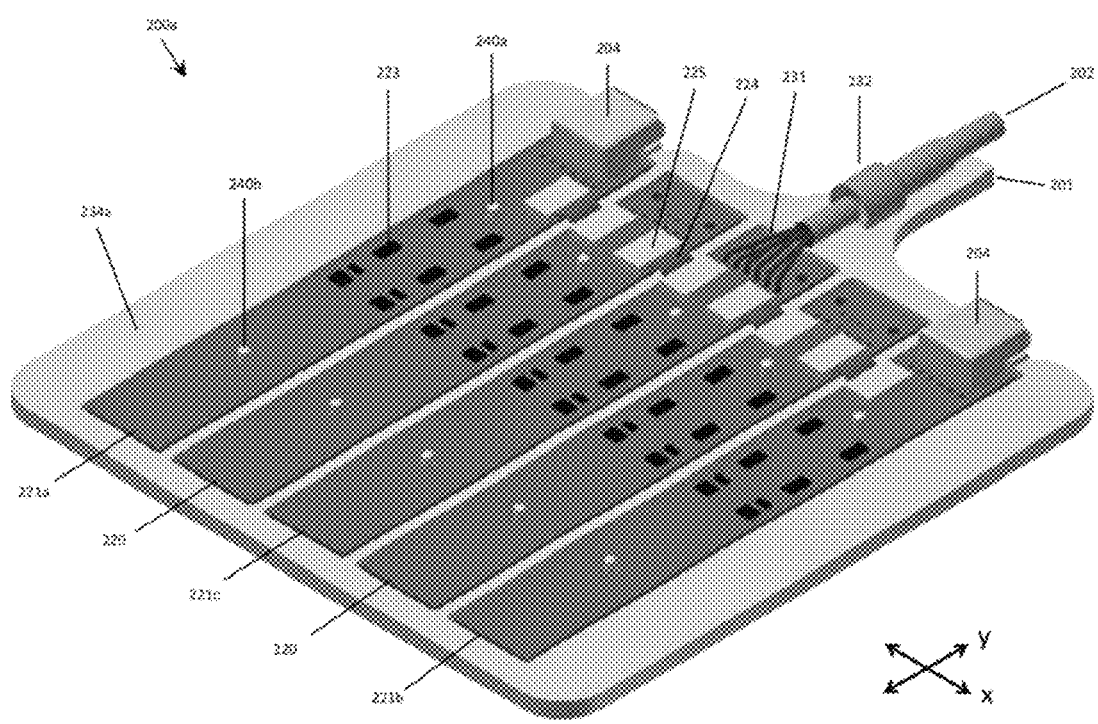
FIG. 25A is a top perspective interior view of the center pad of the disclosed flexible LED pads including the PCBs contained within the pad and an integrated connector cable.
Figure 25B:
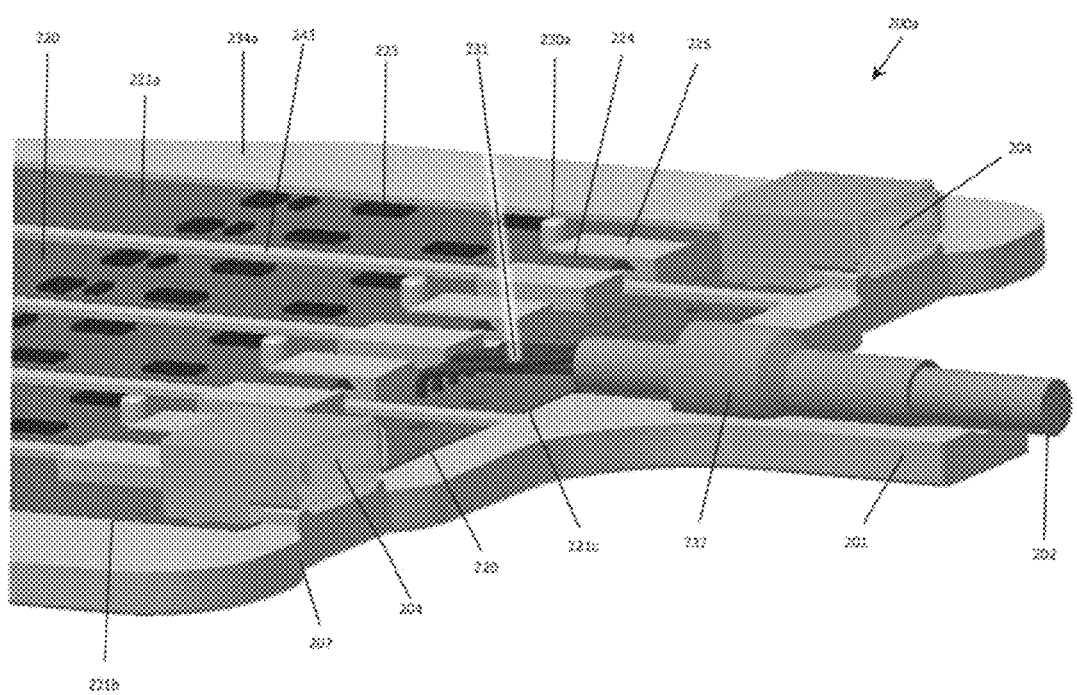
FIG. 25B is a top perspective interior end view of the center pad of the disclosed flexible LED pads including the PCBs contained within the pad, two connector sockets, and an integrated connector cable.

The integration of the PCBs 220 and 221a, 221b and 221c into the bottom piece 234a of center flexible LED pad 220a in illustrated in FIG. 25A in a manner similar to that of the edge flexible LED pad 220b shown in FIG. 20A, except for the inclusion of cable 202 and strain relief 201. Strain relief 201 comprises an extension of the bottom polymeric piece 234a in a direction parallel to the y-axis having a molded slot in which wire 202 is positioned and a deeper notch where wire collar 232 fits snugly. A top piece of center flexible LED pad 200a (not shown) has a mirror image shape to that of stress relief 201, and when glued to bottom polymeric piece 234a, holds wire 202 and wire collar 232 firmly in place to prevent any pulling force stress on the solder joints between the conductive traces on PCB 221c and the discrete wires 231 coming from cable 202. Like the PCBs in the corresponding edge LED pad 200b, the PCBs 221a-221c and 220 are down set into the polymeric bottom piece 234a of flexible LED pad 200a with polymeric ridge 243 to prevent movement of the PCBs 221a-221c and 220 within the LED pad 220a, and further secured by the polymeric posts 240a and 240b protruding through holes in the PCBs and attaching to the top piece of flexible LED pad 200a (not shown in FIG. 25A). FIG. 25B provides a close-up view of cable 202 and cable collar 232, and its position within strain relief 201 of polymeric bottom piece 234a to prevent damage from the solder joints between discrete wires 231 and center PCB 221c.

While tests have revealed the improved reliability of this center flexible LED pad compared to prior art flexible LED pads, it is still possible to damage the solder joints and electrical interconnections between discrete wires 231 and center PCB 221c through compressive forces, e.g. squeezing, pushing, or lying on that portion of LED pad 200b so that wires 231 are moved, flattened, broken or damaged.

Alternative Embodiment of Improved Flexible LED Pad

Figure 26A:
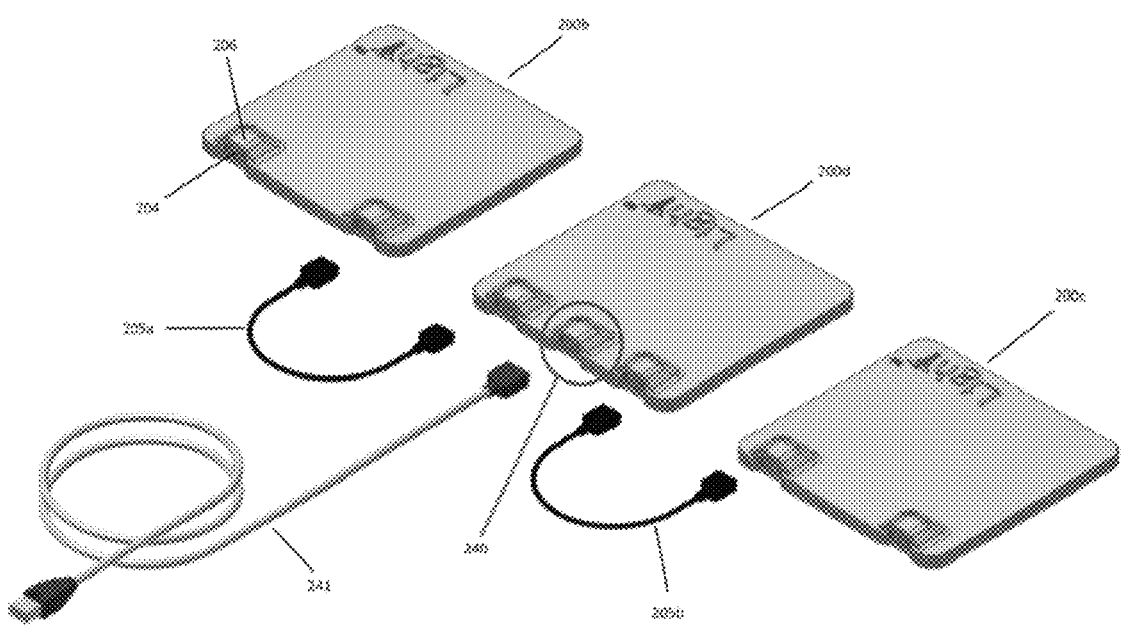
FIG. 26A is a plan view of an alternative embodiment of the disclosed flexible LED pad comprising one center and two side pads, and three unplugged connectors.
Figure 26B:
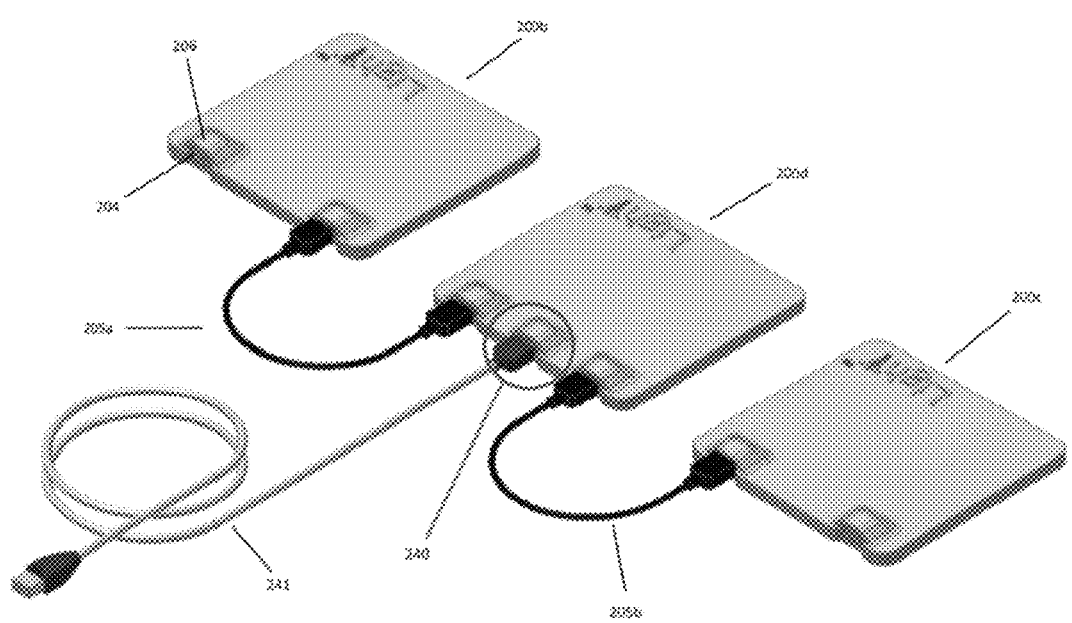
FIG. 26B is a plan view of an alternative embodiment of the disclosed flexible LED pad comprising one center and two side pads, and three connectors connected in a T configuration.

In order to completely eliminate the risk of wire breakage in a flexible set of LED pads used for phototherapy, the only sure means to prevent wire breakage is to completely eliminate discrete wires. Such an approach is illustrated on FIG. 26A where the center LED pad 200d eliminates attached cable 202 and replaces it with long USB cable 241. To facilitate connection from USB cable 241 to flexible LED pad 200d, a third USB socket 204 is introduced into LED pad 200d in location 240, between the standard USB socket locations. As shown in FIG. 26B, to complete electrical connections to the LED pads, USB cables 205a and 205b are employed in the same manner as described above to electrically connect center flexible LED pad 200d to flexible LED pads 200b and 200c respectively, and by connecting long USB cable 241 into third USB socket 240 to facilitate a T configuration pad set.

While the opposite end of USB cable 241 could be custom made with a molded in-line RJ45 connector, it is preferable to employ standard high volume USB cables with male USB plugs on both ends molded into the wire to prevent wire breakage at the cable to plug interface. The termination of cable 241 with a USB plug is incompatible with the existing LED controllers already operating commercially. This issue is addressed later in the disclosure.

Figure 27:
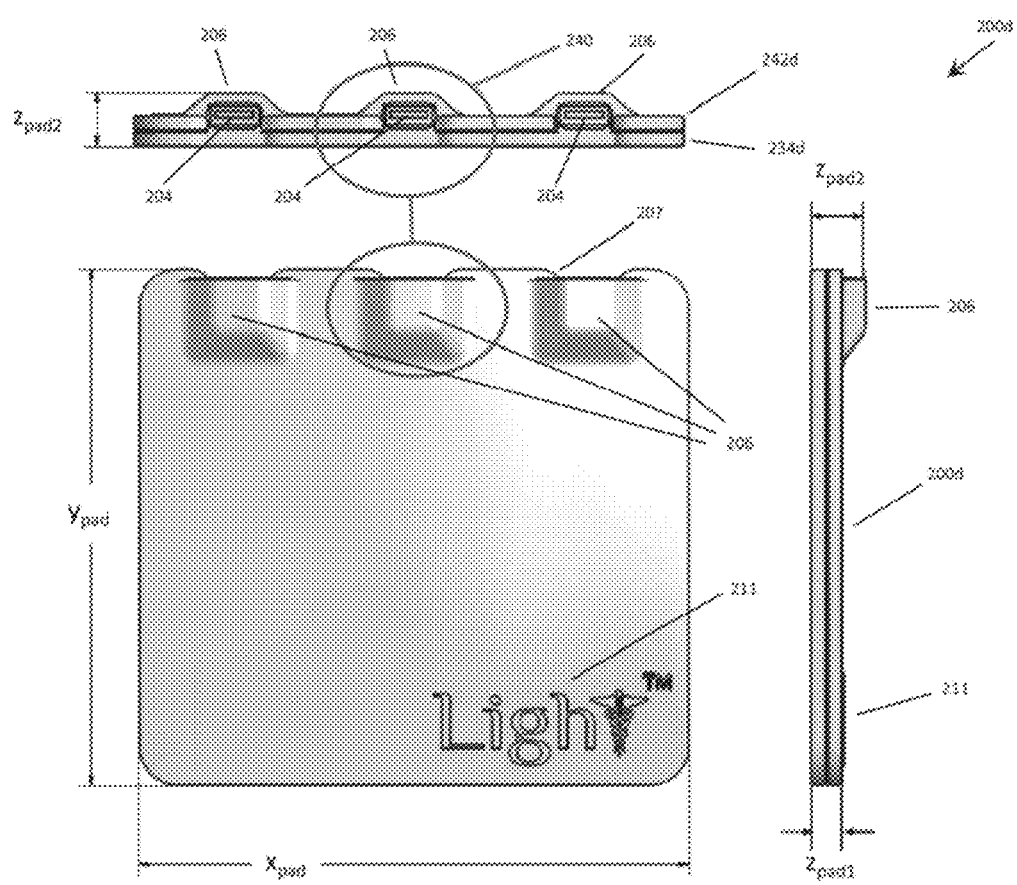
FIG. 27 is a top and edgewise view of the center pad of an alternative embodiment of the disclosed flexible LED pads including representative dimensions.

Detail of the inclusion of the third USB socket 240 in this alternate embodiment of art improved flexible LED pad is shown in the edgewise, lengthwise and top view of FIG. 27. As shown, details of the third USB socket 240 are essentially identical to that of the USB sockets 204, having a bump 206 and an inset 207, except that it is positioned in the center of the edge of the LED pad rather than on the left and right sides. The thickness $z_{pad2}$ of bump 206, e.g. 15 mm, is necessarily thicker than pad thickness $z_{pad1}$ elsewhere, e.g. 8 mm. The extra thickness, nearly double as shown, is needed to insure USB socket 204 is held securely in place and does not delaminate from the polymeric pad molding. Note that the thickness of embossed logo 211 may also be slightly greater than the thickness $z_{pad1}$. As a reference, the rectangular, but nearly square LED pad shown has dimensions $x_{pad}$ and $y_{pad}$ of 137 mm and 142 mm respectively. FIG. 27 also illustrates flexible LED pad actually comprises a top piece 242d and a corresponding bottom piece 234d glued or attached to form a completed center flexible LED pad 200d.

Figure 28:
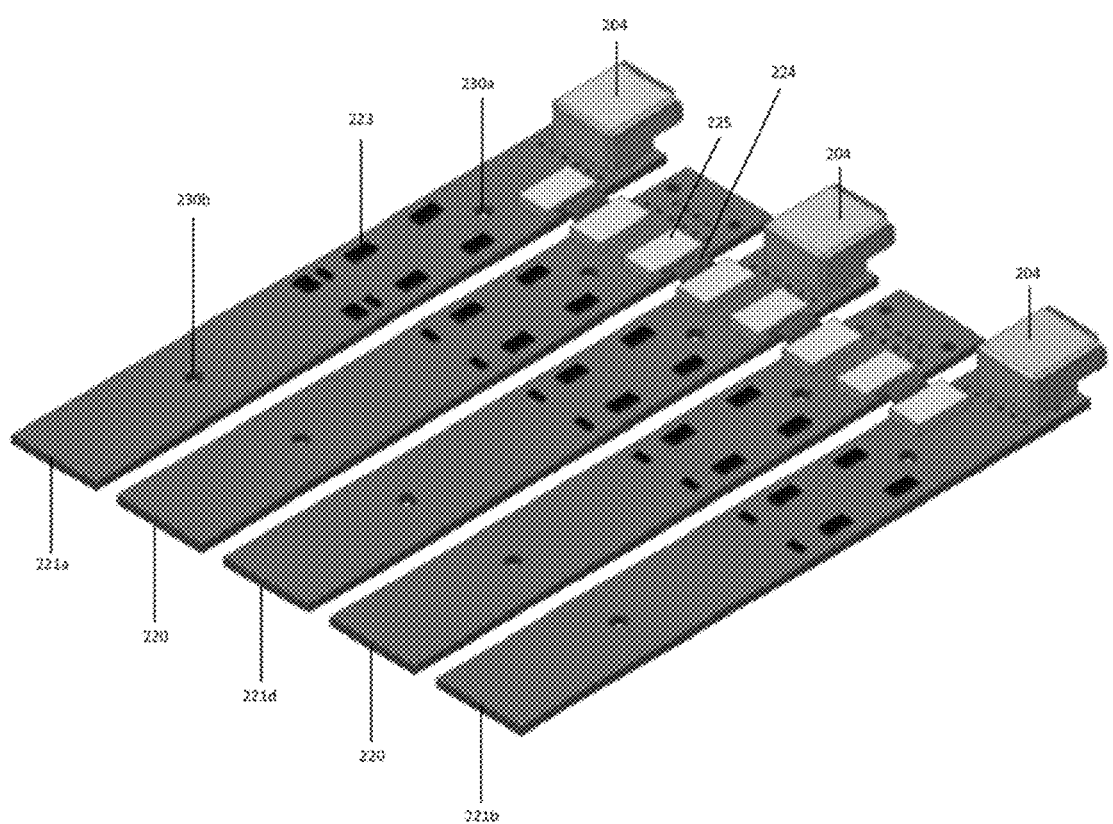
FIG. 28 is a top perspective view of the PCBs contained within an alternative embodiment of the disclosed flexible LED pads including ribbon-cable connectors.
Figure 39:
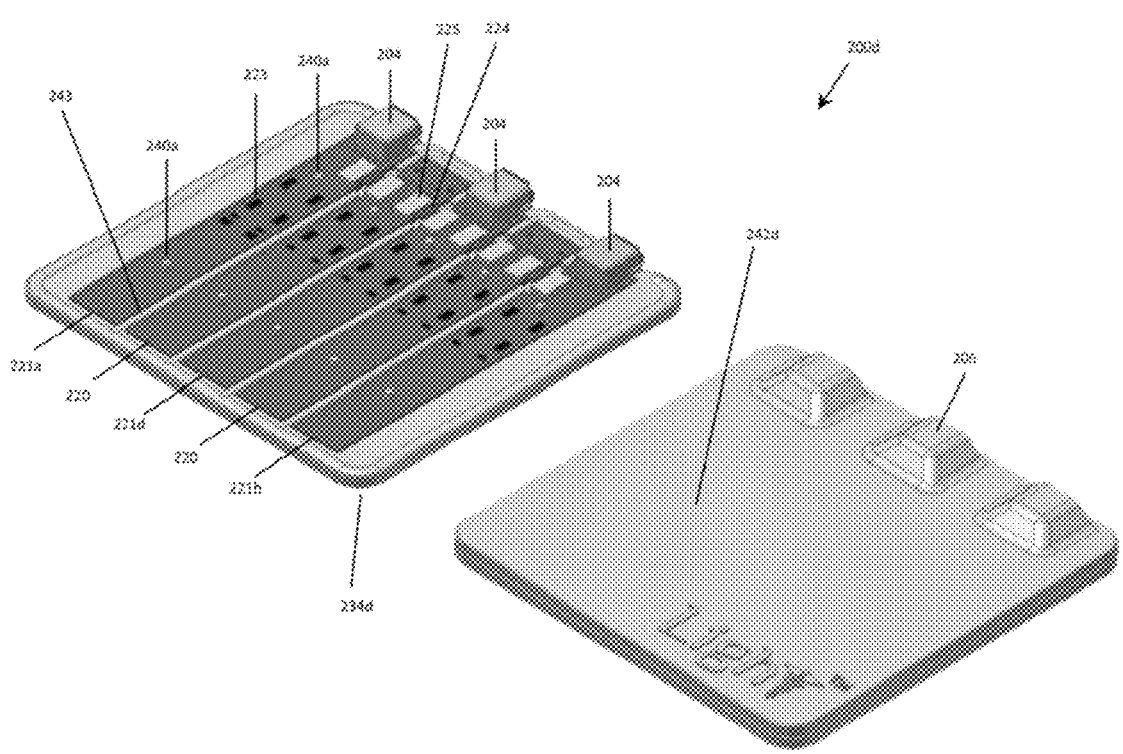

FIG. 28 illustrates the array of PCBs enclosed within center flexible LED pad 200d including in sequential order from left to right, left PCB 221a, symmetric PCB 220, center PCB 221d, symmetric PCB 220, and right PCB 221b. The PCBs are electrically connected through ribbon cables 224 plugged into low profile ribbon cable sockets 225. Every PCB includes holes 230a and 230b for polymeric posts and surface mount components 223. PCBs 221a, 221b and 221d include USB sockets 204. Since the USB sockets 204 and the ribbon-cable sockets 225 all have stiff pins soldered into the PCBs, no loose or flexible wires are soldered onto the PCBs anywhere in the assembly shown.

FIG. 29 illustrates a top view of the aforementioned assembly of PCBs positioned into the bottom polymeric piece 234d of flexible LED pad 200d, where the polymeric posts 240a and 240b protrude through holes 230a and 230b in the PCBs, securing them from moving within the LED pad and keeping the LED array aligned with the holes in the bottom polymeric piece 234d (not visible in FIG. 29). Polymeric ridges 243 also help hold the PCBs in place. The top view of the completed center flexible LED reveals the top piece 242d of flexible LED pad 200d including three bumps 206 for the USB connectors. As described further below, the bottom piece 234d and top piece 242d are glued together in the assembly of pad 200d.

Figure 30:
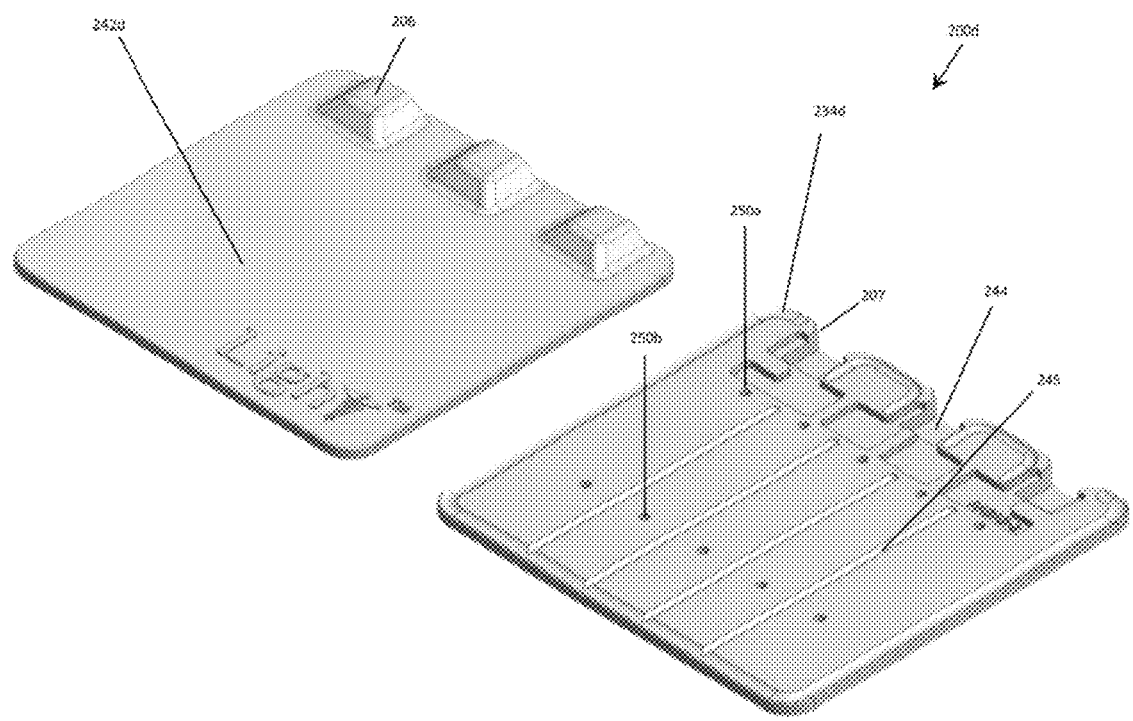
FIG. 30 is a top and underside perspective view of the top piece of center pad of an alternative embodiment of the disclosed flexible LED pads.

FIG. 30 illustrates in top and underside perspective drawing the top piece 242d of center flexible LED pad 200d. While the top view reveals bumps 206, the underside view reveals the intricate shape to fit atop the bottom piece of the LED pad and the PCBs it holds. For example, from the underside view bump 206 forms a cavity 244 to accommodate USB sockets 204. Similarly, holes 250a and 250b are positioned in correspondence to the locations of polymeric posts 240a and 240b in bottom piece 2344d such that posts 240a and 240b fit into holes 250a and 250b when pad 200d is assembled locking the PCBs into place. This is further assisted by groove 245, which is positioned in correspondence to the ridges 243 surrounding the PCBs in the bottom piece 234d of the LED pad 200d.

Figure 31:
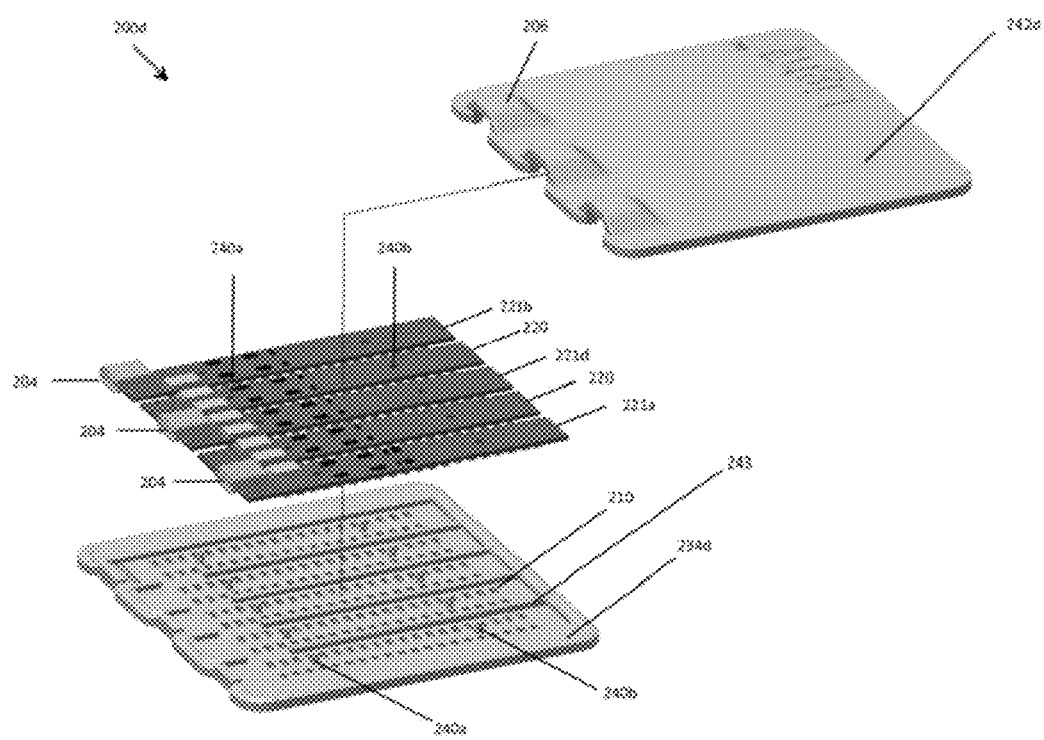
FIG. 31 is an exploded perspective view of the center pad of an alternative embodiment of the disclosed flexible LED pads illustrating the top and bottom pad pieces and the PCBs contained within.

The assembly of the top piece 242d to bottom piece 234d and the intervening PCBs 220 and 221, and USB sockets 204 are shown in expanded view in FIG. 31. The bottom piece 234d contains the holes 210, which are aligned to the LEDs attached to the bottom surfaces of the PCBs 220 and 221, as well as polymeric posts 250a and 250b and polymeric ridge 243. During assembly of flexible LED pad 200d, bottom piece 234d is attached to top pad piece 242d with PCB 221d (and others held within the intervening cavity formed between the pad pieces. In its manufacturing assembly bottom piece 234d is coated with glue, e.g. epoxy, on any surface intended to contact top piece 242d.

Figure 32:
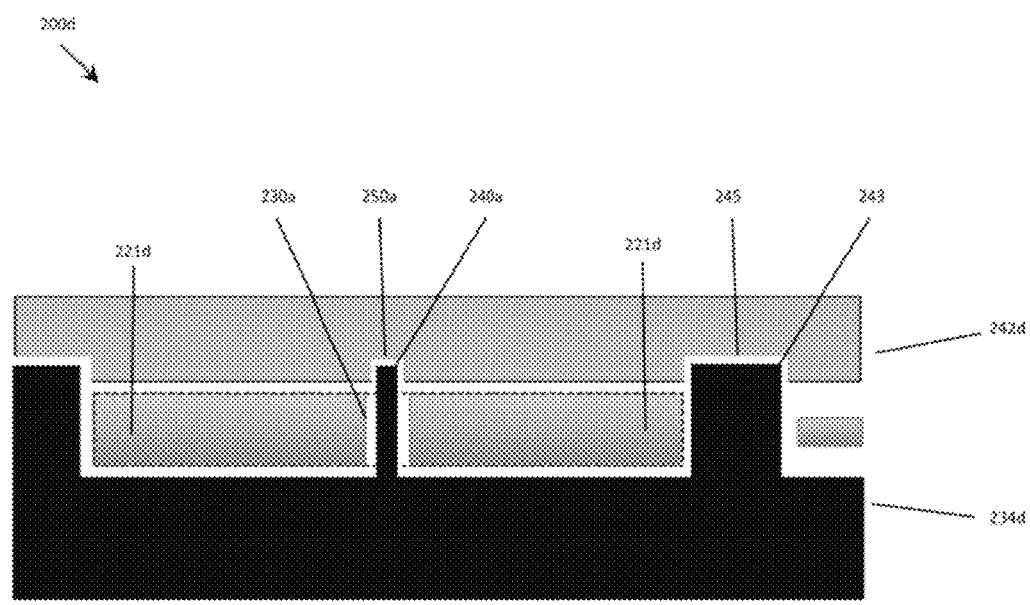
FIG. 32 is an edge cut view illustrating the alignment of the polymeric bottom and top pieces including polymeric posts and ridges to the intervening PCBs.

As shown in FIG. 32, polymeric post 240a (a feature of bottom pad piece 234d) protrudes through hole 230a in PCB 221d and into hole 250a within top pad piece 242d and is glued in place. Similarly, polymeric ridge 243 (also a feature of bottom pad piece 234d) extends upward in the space between PCBs and into slot 245 within top pad piece 242d and is glued in place. After assembly, time is required for the epoxy or glue bonding the top and bottom pieces to cure or dry before the pad can be moved or disturbed. The curing or drying time can range from several hours to one day in duration. After completion, the result is that PCB 221d and all other PCBs cannot move laterally unless the polymeric material comprising flexible LED pad 200d is ripped or damaged.

The other LED pads described above, e.g., LED pads 200a, 200b and 200c, and the components they contain, are assembled in a manner similar to LED pad 200d.

Another aspect of the disclosed flexible LED pad design is the use of Velcro straps attached to Velcro belt in order to position and hold the pads in a fixed position for extended durations during treatments, in some cases over one hour. Attachment of Velcro tape onto the aseptic, hypoallergenic, biologically inert polymeric pads has proven to be extremely problematic because of the material mismatch between the plasticized backside of Velcro tape and the pad itself. In essence, the very feature that prevents the pad from reacting chemically or biologically is the root cause of its inability to firmly bond with general purpose adhesives, meaning glues that attach strongly to the Velcro tape backing do not bond with polymeric pad materials, such as silicone, polytetrafluoroethylene (Teflon), etc. Conversely, glues and epoxies designed to bond to the polymeric pad do not bond to the plasticized backing of Velcro tape. In use, pulling the Velcro belt off of the Velcro straps frequently rips the Velcro straps off of the polymeric pad.

Figure 33:
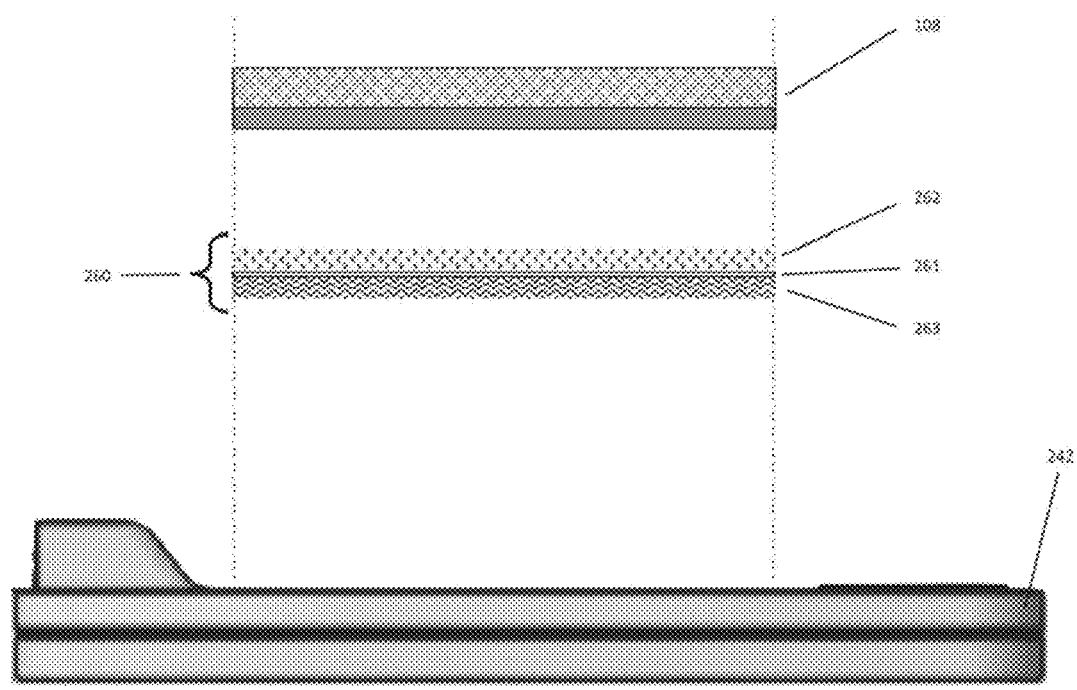
FIG. 33 is a cross sectional schematic of method to attach Velcro to the surface of a polymeric pad.

One solution to this incompatibility relies on the use of an intermediate layer coated on opposite sides with two different kind of adhesives. As shown in FIG. 33, polymeric pad 242 comprising a non-reactive material such as Teflon or silicone is attached to a Velcro tape 108 with a special adhesive tape 260 comprising a polyester film 261 coated on one side with a silicone glue or epoxy 263, and other the other side by an acrylic-based glue 262. Silicone adhesive 263 forms a strong adhesive chemical bond to polymeric pad 242 and to interposing polyester film 261. Acrylic-based adhesive 262 forms a strong adhesive bond to the plasticized backside of Velcro 108. So long as both adhesive layers 262 and 261 form a strong adhesive bond to interposing polyester layer 261 the disclosed, method insures Velcro strap can securely be onto polymeric pad 242.

Electrical Considerations of LED Pad Design

Figure 34A:
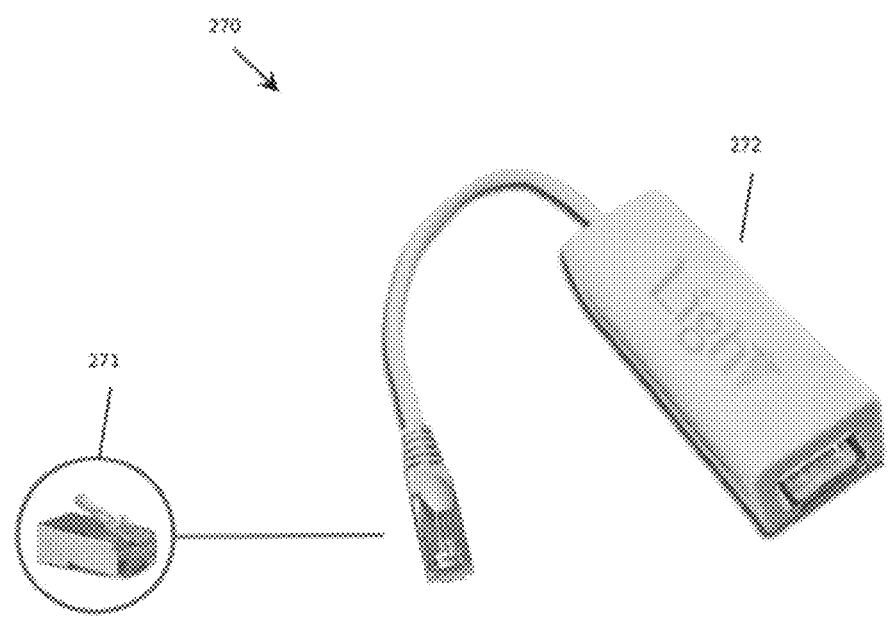
FIG. 34A is a pictograph of a customized adapter for convening a USB plug, to an RJ45 plug

Aside from the mechanical aspects and their impact on the reliability on LED pad operation, the flexible LED pad must electrically connect to the LED controller units to receive power and control signals. As illustrated previously in FIG. 26A, USB cable 241 has a USB plug on each end and is incompatible with existing LED controllers units having RJ45 sockets. To avoid noise issues, however, it is mandatory that a shielded RJ45 plug and shielded socket are used such as shown by example in FIG. 34A, which shows a cable connected to a RJ45 plug 271 on one end and to a USB socket on the other end.

Figure 34B:
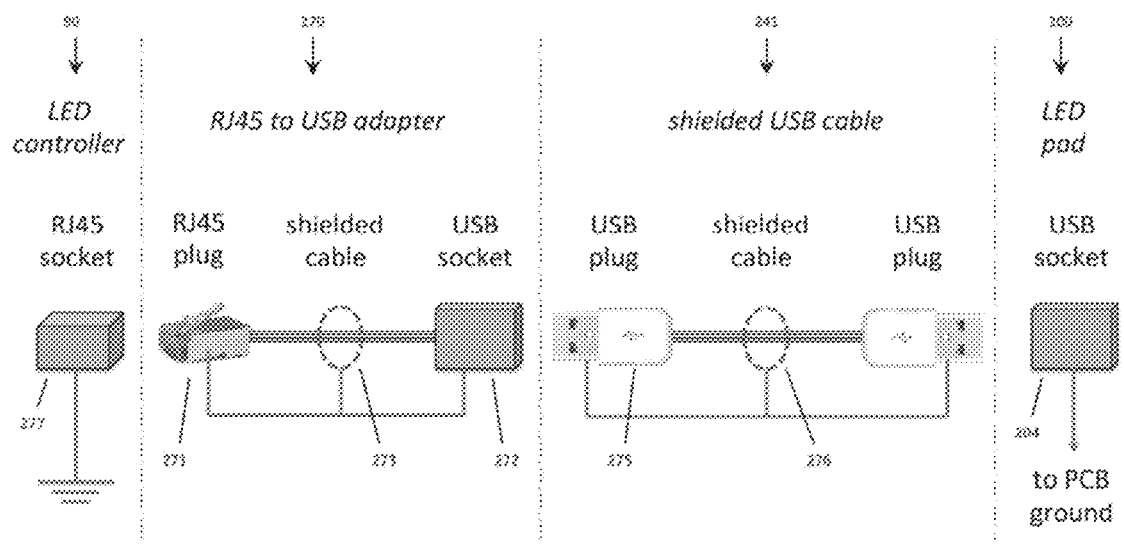
FIG. 34B is a method for shielding long cables and LED pads from noise in phototherapy applications.

The schematic diagram of FIG. 34B shows an LED pad 200 connected to an LED controller 90 through a shielded USB cable 241 and an RJ45-to-USB adapter 270. As shown, the socket shield 277 within LED controller 90 must be grounded to the case of the LED controller 90 and power supply. The shielded case of the RJ45 plug 271 is in turn connected to the shield 273 within the cable of adapter 270 and ultimately connected to the shield of USB socket 272. When USB cable 241 is plugged into USB adapter socket 272 the ground is connected to the USB cable shielding 276 and ultimately to the around connection within the flexible LED pads 200 through USB socket 204.

While the primary purpose of RJ45-to-USB adapter 270 is to facilitate a means by which to use high quality molded shielded USB cable 241 to connect LED controller 90 to LED pad 200, it offers other benefits. First by requiring use of the adapter to connect shielded USB cable 241 to LED controller 90, there is no accidental way for anyone to inadvertently connect a USB device or peripheral such as a USB battery charger, USB memory, or USB speakers to LED controller 90 without intentionally inserting RJ45-to-USB adapter 270 in between. The instructions for use of the RJ45-to-USB adapter 270 can then be clearly labeled warning all users that it is not to be used to connect USB peripherals of any other device other than the LED pad 270 to LED controller 90. A warning label can even be affixed directly onto the RJ45-to-USB adapter's cable itself.

The second benefit of the adapter is to reduce the risk of damage caused by anyone tripping over the shielded USB cable 241. While the RJ45 plug and socket are locked into place by tabs upon plug insertion, the USB socket in RJ45-to-USB adapter 270 can be chosen to be the non-locking type. In the event anyone trips on shielded USB cable 243, the USB cable plug easily is dislodged from RJ45-to-USB adapter 270 without tripping the passer-by and without pulling LED controller 90 of the table and causing damage to the device.

Figure 35A:
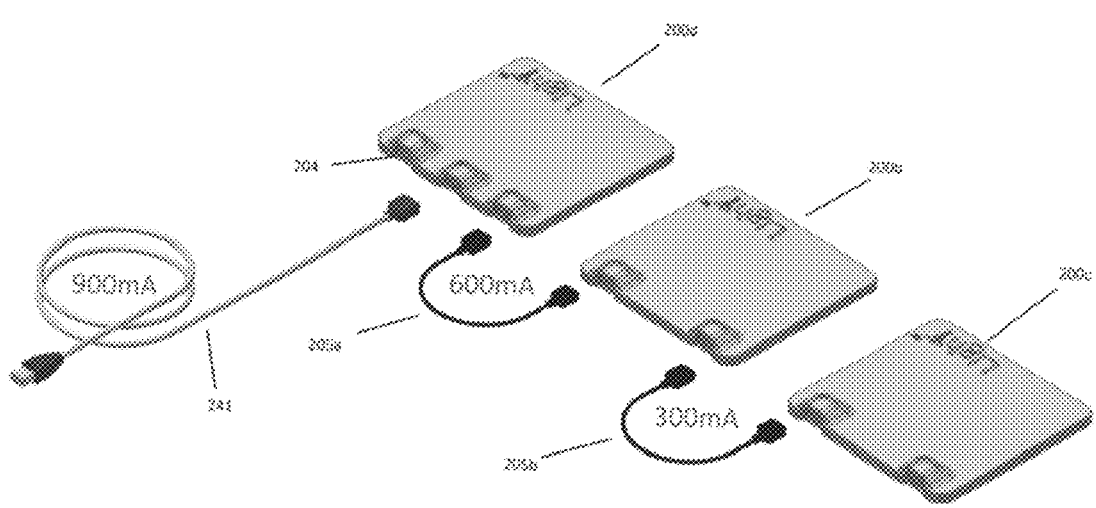
FIG. 35A is a schematic representation of a set of three flexible LED pads in an L-configuration.

It is also important to insure shielded USB cable 241 can handle the requisite current to drive up to three LED pads, i.e. one LED pad set across a single USB cable. When considering current capability of an LED pad set, there is no way to prevent a clinician from connecting the LED pads in an L configuration as shown in FIG. 35A, one where the connector from the flexible LED pad 200d (which is designed to be connected between LED pads 200b and 200c) must supply all the current through two LED pads 200b and 200c. As shown, cable 241 carries a maximum current 900 mA, the sum of all three LED pads' peak current consumption. USB cable 205a supplies all the current for two LED pads, namely 600 mA for pads 200b and 200c. USB cable 205b need only carry 300 mA for LED pad 200c. While USB cables can easily handle that amount of current and more, care must be given to the ribbon cable connectors bridging one PCB to the next with the flexible LED pads.

Figure 35B:
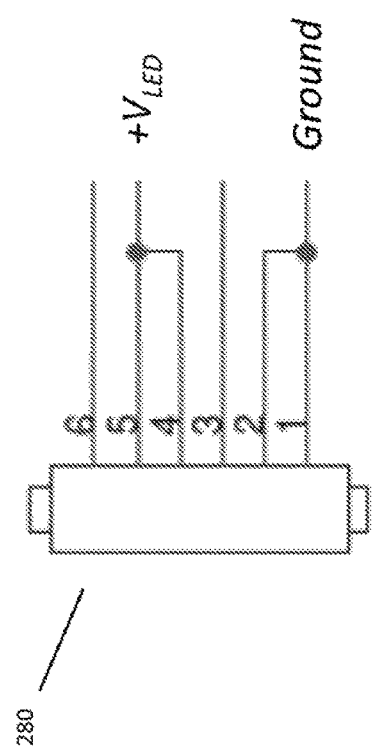
FIG. 35B illustrates the current handling capability of the PCB-to-PCB ribbon cable.

Assuming cable 241 is plugged into the center USB socket of flexible LED pad 200d, then 150 mA of the pad's total current will be flowing to the left side of the LED pad 200d and 150 mA will be flowing to the right side of LED pad 200d. This 150 mA, along with 600 mA required for LED pads 200b and 200c means the PCB-to-PCB ribbon cable (not shown) connecting the two ribbon cable sockets in LED pad 200d must carry a worst case total current of 750 mA. Each copper conductor in ribbon cable 224 can carry a steady state value over 400 mA. So as schematic diagram 280 in FIG. 35B illustrates, by shorting two cables together for parallel conduction in the power lines $+V_{LED}$ and ground, the ribbon cable can carry 800 mA and is able to handle the current even if the LED pads are connected in an L configuration.

We claim:

1. A flexible LED pad for use in phototherapy comprising a plurality of rigid printed circuit boards (PCBs) arrayed in a row across the pad, an array of LEDs being attached to each PCB, each of the PCBs having mounted thereto an electrical connector, a ribbon cable extending between the electrical connector on one of the PCBs and the electrical connector on an adjacent one of the PCBs, the PCBs, the electrical connectors and the ribbon cable being enclosed in a flexible material.

2. The flexible LED pad of claim 1 wherein the plurality of rigid PCBs comprise a first PCB and a second PCB, a first electrical connector on the first PCB being mounted at a first edge of the first PCB facing a first edge of the second PCB, a second electrical connector on the second PCB being mounted on the first edge of the second PCB facing the first edge of the first PCB, a first cable connector at a first end of the ribbon cable being mated with the first electrical connector, a second cable connector at a second end of the ribbon cable being mated with the second electrical connector.

3. The flexible LED pad of claim 2 wherein each of the electrical connectors comprises a socket.

4. The flexible LED pad of claim 3 wherein each of the cable connectors comprises a plug compatible with the socket.

5. The flexible LED pad of claim 4 further comprising an external electrical connector mounted on a second edge of the first PCB, the external electrical connector being for linking the flexible LED pad to a second flexible LED pad.

6. The flexible LED pad of claim 5 wherein the external electrical connector comprises a USB socket.

7. The flexible LED pad of claim 6 wherein the flexible material comprises a top piece and a bottom piece, the bottom piece comprising a downset for each of the first and second PCBs, each PCB being fitted into a corresponding downset in the bottom piece.

8. The flexible LED pad of claim 7 wherein the bottom piece comprises a plurality of openings, each of the openings being aligned with one of the LEDs.

9. The flexible LED pad of claim 8 wherein each of the first and second PCBs comprises at least one hole, a post extending from one of the top and bottom pieces through the at least one hole to assist in anchoring the PCB at a selected position within the flexible material.

10. The flexible LED pad of claim 9 wherein the post extends into a hole formed in the other of the top and bottom pieces.

11. The flexible LED pad of claim 8 wherein the top piece and the bottom piece are glued together so as to enclose the first and second PCBs.

12. The flexible LED pad of claim 4 wherein the flexible material comprises a strain relief formed along an edge of the flexible LED pad, a feature being formed in the strain relief for mating with a corresponding feature on a cable linking the LED pad with a control unit.

13. The flexible LED pad of claim 4 further comprising an external electrical connector mounted on a second edge of the first PCB, the external electrical connector being for linking the flexible LED pad to an LED control unit.

14. The flexible LED pad of claim 13 wherein the external electrical connector comprises a USB socket.

15. The flexible LED pad of claim 1 further comprising a Velcro tape attached to the flexible material by means of an adhesive film, the adhesive film being attached to the flexible material by a first adhesive material and being attached to the Velcro tape by a second adhesive material.

16. The flexible LED pad of claim 15 wherein the flexible material comprises a polymeric material and the first adhesive material comprises a silicone glue or epoxy.

17. The flexible LED pad of claim 16 wherein the second adhesive material comprises an acrylic-based adhesive.

18. The flexible LED pad of claim 17 wherein the adhesive film comprises a polyester film.

19. An arrangement comprising a plurality of flexible LED pads for use in phototherapy, each of the flexible LED pads comprising a plurality of rigid printed circuit boards (PCBs) arrayed in a row across the pad, an array of LEDs being attached to each PCB, each of the PCBs having mounted thereto an electrical connector, a ribbon cable extending between the electrical connector on one of the PCBs and the electrical connector on an adjacent one of the PCBs, the PCBs, the electrical connectors and the ribbon cable being enclosed in a flexible material, an LED control unit and a control cable linking one of the flexible LED pads to the LED control unit, said one of the flexible LED pads comprising an electrical connector mated to a corresponding electrical connector at an end of the control cable.

20. The arrangement of claim 19 wherein the electrical connector comprised in said one of the flexible LED pads comprises a USB socket and the electrical connector at the end of the control cable comprises a USB plug.

21. The arrangement of claim 20 wherein the control cable further comprises an adapter cable connected to the LED control unit.

22. The arrangement of claim 21 wherein the adapter cable comprises a USB connector at one end of the adapter cable and a RJ45 plug at the opposite end of the adapter cable.

23. The arrangement of claim 19 wherein the control cable is shielded.

24. The arrangement of claim 19 wherein each of the flexible LED pads has a rectangular shape and each of the flexible LED pads comprises second and third electrical connectors positioned along a single edge of the rectangular shape, at least one of the second and third connectors in each flexible LED pad being connected to a cable extending to an adjacent flexible LED pad in the arrangement.

25. The arrangement of claim 24 wherein the flexible LED pads and the LED control unit are arranged in a T configuration.

26. The arrangement of claim 24 wherein the flexible LED pads and the LED control unit are arranged in an L configuration.

* * * * *